(12) United States Patent
Mattei et al.

(10) Patent No.: US 6,696,467 B2
(45) Date of Patent: Feb. 24, 2004

(54) QUINOLINE DERIVATIVES

(75) Inventors: Patrizio Mattei, Riehen (CH); Werner Mueller, Aesch (CH); Werner Neidhart, Hagenthal le Bas (FR); Matthias Heinrich Nettekoven, Grenzach-Wyhlen (DE); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/358,006

(22) Filed: Feb. 4, 2003

(65) Prior Publication Data

US 2003/0153553 A1 Aug. 14, 2003

(30) Foreign Application Priority Data

Feb. 4, 2002 (EP) .............................. 02001967

(51) Int. Cl.$^7$ ...................... A61K 31/46; C07D 215/38
(52) U.S. Cl. ...................... 514/313; 546/159; 546/160; 546/162
(58) Field of Search ................. 546/159, 160, 546/162; 514/313

(56) References Cited

U.S. PATENT DOCUMENTS

| | | | |
|---|---|---|---|
| 4,035,367 A | | 7/1977 | Simpson |
| 4,598,089 A | * | 7/1986 | Hadvary et al. ............ 514/449 |
| 4,931,463 A | | 6/1990 | Barbier et al. |
| 4,983,746 A | | 1/1991 | Barbier et al. |
| 5,399,720 A | | 3/1995 | Karpf et al. |
| 6,004,996 A | * | 12/1999 | Shah et al. .................. 514/449 |
| 6,573,263 B2 | * | 6/2003 | Niewhner et al. .......... 514/243 |

FOREIGN PATENT DOCUMENTS

| | | |
|---|---|---|
| EP | 0 185 359 | 6/1986 |
| EP | 0 189 577 | 8/1986 |
| EP | 0 443 449 | 8/1991 |
| EP | 0 524 495 | 1/1993 |
| WO | WO 96 37474 | 11/1996 |
| WO | WO 99/34786 | 7/1999 |
| WO | WO 00/09122 | 2/2000 |
| WO | WO 00/09123 | 2/2000 |
| WO | WO 02 20488 | 3/2002 |
| WO | WO 02 094789 | 11/2002 |

* cited by examiner

*Primary Examiner*—D. Margaret Seaman
(74) *Attorney, Agent, or Firm*—George W. Johnston; Dennis P. Tramaloni; Eileen M. Ebel

(57) ABSTRACT

Compounds of general formula I

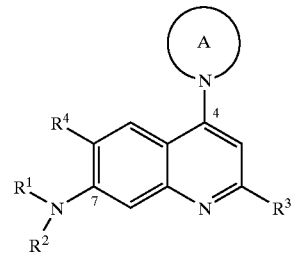

as well as pharmaceutically acceptable salts and esters thereof, are potent inhibitors of neuropeptide Y and can be used in the form of pharmaceutical preparations for the treatment or prevention of various disease states and related morbidities including obesity.

22 Claims, No Drawings

QUINOLINE DERIVATIVES

BACKGROUND OF THE INVENTION

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropetide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on con associated risk factors such as arthritis, cardiovascular diseases, diabetes and renal failure.

SUMMARY OF THE INVENTION

The present invention is concerned with novel quinoline derivatives useful as neuropeptide Y (NPY) receptor ligands, particularly neuropeptide Y (NPY) antagonists. More particularly, the present invention discloses compounds of the general formula

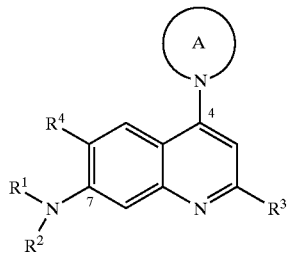

and the pharmaceutically acceptable salts and esters thereof, and their use in the form of pharmaceutical preparations for the treatment or prevention of various disease states and related morbidities including obesity.

DETAILED DESCRIPTION OF THE INVENTION

The present invention comprises compounds of the formula

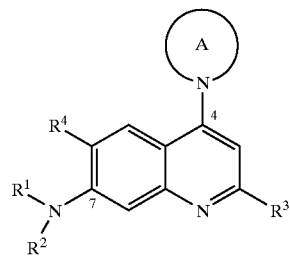

(I)

wherein
$R^1$ and $R^2$ are independently selected from hydrogen, alkyl, cycloalkyl, cycloalkylalkyl, alkylcarbonyl, cycloalkylcarbonyl, cycloalkylalkylcarbonyl, aryl, aralkyl, arylcarbonyl, aralkylcarbonyl, alkoxyalkyl, hydroxyalkyl, heterocyclyl, heterocyclylalkyl, heterocyclylcarbonyl, heterocyclylalkylcarbonyl, carbocyclyl, carbocyclylalkyl, amino, alkyl-$SO_2$—, aryl-$SO_2$—, heterocyclyl-$SO_2$— or amino-$SO_2$— or $R^1$ and $R^2$ together with the N atom to which they are attached form a 5- to 10-membered heterocyclic ring which optionally comprises a second heteroatom selected from nitrogen or oxygen and, wherein the heterocyclyc ring is optionally substituted with one or more substituents independently selected from alkyl and alkoxy;
$R^3$ is hydrogen, alkyl, amino or halogen;
$R^4$ is hydrogen, halogen, heterocyclyl, amino or alkyl;
A is a 5 to 7-membered saturated heterocyclic ring comprising the nitrogen atom which is attached to the quinoline ring and optionally a second heteroatom which is selected from oxygen, sulfur or nitrogen and, wherein the ring A is optionally substituted by one to three substituents independently selected from alkyl, alkoxy, hydroxy, amino, acetylamino, cyano, hydroxyalkyl, alkoxyalkyl, cycloalkylalkoxy and cycloalkylalkoxyalkyl; and pharmaceutically acceptable salts and esters thereof.

The compounds of formula I and their pharmaceutically acceptable salts and esters are novel and have valuable pharmacological properties. They are neuropeptide ligands, for example neuropeptide receptor antagonists and in particular, they are selective neuropeptides Y Y5 receptor antagonists.

Accordingly, the compounds of formula I, their salts and esters can be used in the prophylaxis or treatment of of arthritis, cardiovascular diseases, diabetes, renal failure and particularly eating disorders and obesity.

Objects of the present invention are the compounds of formula I and their aforementioned salts and esters per se and their use as therapeutically active substances, a process for the manufacture of the said compounds, intermediates, pharmaceutical compositions, medicaments comprising the said compounds, their pharmaceutically acceptable salts and esters, the use of the said compounds, salts and esters for the prophylaxis and/or therapy of illnesses, especially in the treatment or prophylaxis of arthritis, cardiovascular diseases, diabetes, renal failure and particularly eating disorders such as hyperphagia and particularly obesity, and the use of the said compounds, salts and esters for the production of medicaments for the treatment or prophylaxis of arthritis, cardiovascular diseases, diabetes, renal failure and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxy preferably methoxy and ethoxy and most preferred methoxy.

The term "aryl", alone or in combination, signifies a phenyl or naphthyl group, preferably a phenyl group which optionally carries one or more, particularly one to three substituents each independently selected from halogen, trifluoromethyl, amino, alkyl, alkoxy, aryloxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitrol and the like. Preferred substituents of aryl, preferably phenyl are independently selected from halogen, trifluoromethyl, alkyl, alkoxy, cyano and nitro. Examples of aryl are phenyl, cyanophenyl, methoxyphenyl, fluorophenyl and methylphenyl.

The term "aralkyl", alone or in combination, signifies an alkyl or cycloalkyl group as previously defined, which is substituted with one or more, preferably one or two, particularly preferred one aryl group and, wherein the term aryl is defined as before. Examples are benzyl, benzyl substituted with hydroxy, alkoxy or halogen, preferably fluorine.

The term "heterocyclyl", alone or in combination, signifies a saturated, partially unsaturated or aromatic 4- to 10-membered heterocycle which contains one or more, preferably one ore two hetero atoms selected from nitrogen, oxygen and sulfur, wherein oxygen and particularly nitrogen are preferred. If desired, it can be substituted on one or more carbon atoms by halogen, alkyl, alkoxy, oxo, alkoxyalkyl, hydroxyalkyl etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyridinyl, furyl, pyrrolidinyl, piperidinyl, morpholinyl, piperazinyl, 3,4-dihydro-1H-isoquinolinyl, thiophenyl and azepanyl, wherein each of these rings can be optionally substituted by one or more, preferably one substituent independently selected from alkyl and halogen. Particularly preferred are pyrrolidinyl, pyridinyl, furyl, thiophenyl and chloro-pyridinyl.

The term "carbocyclyl", alone or in combination, signifies partially unsaturated 4- to 10-membered carbocyclic ring, wherein optionally one or more carbon atoms are substituted by halogen, alkyl, cycloalkyl, alkoxy, oxo, aryl, with alkyl being preferred. An examples of carbocyclyl is indanyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methylethylamino, pyrrolidinyl and piperidino. Particularly preferred primary amino.

The term "cycloalkylalkyl", alone or in combination, signifies an alkyl group which is substituted with one or more, preferably one cycloalkyl group and, wherein the terms alkyl and cycloalkyl have the previously given significance.

The term "cycloalkylalkylcarbonyl" alone or in combination, signifies a cycloalkylalkyl-C(O)— group, wherein cycloalkylalkyl is defined as before.

The term "cycloalkylalkoxy" alone or in combination, signifies an alkoxy group which is substituted with one or more, preferably one cycloalkyl group and, wherein the terms alkoxy and cycloalkyl have the previously given significance.

The term "cycloalkylalkoxyalkyl" alone or in combination, signifies an alkyl group which is substituted with one or more, preferably one cycloalkylalkoxy group and, wherein the terms alkyl and cycloalkylalkoxy have the previously given significance.

The term "heterocyclylalkylcarbonyl", alone or in combination, signifies a heterocyclylalkyl-C(O)— group, wherein heterocyclylalkyl is defined as before.

The term "aralkylcarbonyl", alone or in combination, signifies an aralkyl-C(O)— group, wherein aralkyl is defined as before.

The term "alkylcarbonyl", alone or in combination, signifies an alkyl-(CO)— group, wherein the term alkyl has the previously given significance.

The term "cycloalkylcarbonyl", alone or in combination, signifies a cycloalkyl-(CO)— group, wherein the term cycloalkyl has the previously given significance.

The term "arylcarbonyl", alone or in combination, signifies an aryl-(CO)— group, wherein the term aryl has the previously given significance.

The term "alkoxyalkyl", alone or in combination, signifies an alkyl group which is substituted with one or more, preferably one alkoxy group and, wherein the terms alkyl and alkoxy have the previously given significance.

The term "hydroxyalkyl", alone or in combination, signifies an alkyl group which is substituted with one or more, preferably one hydroxy group and, wherein the terms alkyl and hydroxy have the previously given significance.

The term "heterocyclylalkyl", alone or in combination, signifies an alkyl group which is substituted with one or more, preferably one heterocyclyl group and, wherein the terms alkyl and heterocyclyl have the previously given significance.

The term "heterocyclylcarbonyl", alone or in combination, signifies a heterocyclyl-(CO)— group, wherein the term heterocyclyl has the previously given significance.

The term "carbocyclylalkyl", alone or in combination, signifies an alkyl group which is substituted with one or more, preferably one carbocyclyl group and, wherein the terms alkyl and carbocyclyl have the previously given significance.

The term "halogen" signifies fluorine, chlorine, bromine or iodine and preferably fluorine, chlorine or bromine and particularly chlorine.

The term "cyano", alone or in combination, signifies a —CN group.

The term "nitro", alone or in combination, signifies a —$NO_2$ group.

The term "hydroxy", alone or in combination, signifies a —OH group.

The term "carbonyl" refers to a group of formula —C(O)—.

Examples of pharmaceutically acceptable salts of the compounds of formula I are salts with physiologically compatible mineral acids such hydrochloric acid, sulfuric acid or phosphoric acid; or with organic acids such as methanesulfonic acid, formic acid, acetic acid, trifluoroacetic acid, citric acid, fumaric acid, maleic acid, tartaric acid, succinic acid, salicylic acid and oxalic acid. Preferred are the hydrochloride salts. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes pharmaceutically usable solvates.

The term pharmaceutically acceptable esters of the compounds of formula I means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In the nomenclature used in the present application the ring atoms of the quinoline ring are numbered as follows:

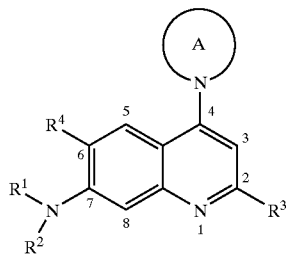

wherein, $R^3$ is attached at the 2-position and $R^4$ is attached at the 6-position.

Preferred are the compounds of formula I and pharmaceutically acceptable salts. Particularly preferred are the compounds of formula I.

Further preferred are the compounds of formula I, wherein $R^1$ and $R^2$ are independently selected from hydrogen, alkyl, cycloalkyl, cycloalkylalkyl, alkylcarbonyl, cycloalkylcarbonyl, aryl, aralkyl, arylcarbonyl, alkoxyalkyl, hydroxyalkyl, heterocyclyl, heterocyclylalkyl, heterocyclylcarbonyl, carbocyclyl, carbocyclylalkyl, amino, alkyl-$SO_2$—, aryl-$SO_2$—, heterocyclyl-$SO_2$— or amino-$SO_2$— or $R^1$ and $R^2$ together with the N atom to which they are attached form a 5- to 10-membered heterocyclic ring which optionally comprises a second heteroatom selected from nitrogen or oxygen and, wherein the heterocyclyc ring is optionally substituted with one or more substituents independently selected from alkyl and alkoxy; and A is a 5 to 7-membered saturated heterocyclic ring comprising the nitrogen atom which is attached to the quinoline ring and optionally a second heteroatom which is selected from oxygen, sulfur or nitrogen and, wherein the ring A is optionally substituted by one to three substituents independently selected from alkyl, alkoxy, hydroxy, amino, acetylamino, cyano, hydroxyalkyl and alkoxyalkyl.

Preferred are compounds according to formula I, wherein $R^3$ is hydrogen or alkyl. Preferred are compounds of formula I, wherein $R^3$ is hydrogen. Further preferred compounds are those, wherein $R^3$ is alkyl. Particularly preferred are compounds of formula I, wherein $R^3$ is methyl.

Also preferred are compounds of formula I, wherein $R^4$ is hydrogen or alkyl. Further preferred are those compounds of formula I, wherein $R^4$ is hydrogen or methyl. Particularly preferred are compounds according to formula I, wherein $R^4$ is hydrogen.

Another preferred aspect of the present invention are compounds according to formula I, wherein $R^4$ is amino, particularly pyrrolidinyl.

Also preferred are compounds according to formula I, wherein A is pyrrolidine or azepane optionally substituted with alkyl, alkoxyalkyl or hydroxyalkyl. Particularly preferred are compounds of formula I, wherein A is pyrrolidine optionally substituted with hydroxymethyl or methoxymethyl.

Preferred are compounds of formula I, wherein A is pyrrolidine or azepane optionally substituted with alkyl, alkoxyalkyl, hydroxyalkyl or alkoxy.

Further preferred are compounds according to formula I, wherein A is pyrrolidine or azepane optionally substituted with alkyl, alkoxy, alkoxyalkyl or hydroxyalkyl. Particularly preferred are compounds of formula I, wherein A is pyrrolidine optionally substituted with hydroxymethyl, methoxymethyl, methoxy or ethoxy.

Another preferred aspect of the present invention are compounds according to formula I, wherein one of $R^1$ and $R^2$ is hydrogen or alkyl and the other is independently selected from alkyl, cycloalkyl, cycloalkylalkyl, alkylcarbonyl, cycloalkylcarbonyl, phenyl, naphthyl, phenylalkyl, naphthylalkyl, phenylcarbonyl, alkoxyalkyl, hydroxyalkyl, thiophenyl, pyridinyl, furyl, thiophenylalkyl, pyridinylalkyl, furylalkyl, thiophenylcarbonyl, pyridinylcarbonyl, furylalkyl, indanyl, carbocyclylalkyl, amino, alkyl-$SO_2$—, aryl-$SO_2$—, thiophenyl-$SO_2$—, pyridinyl-$SO_2$—, furyl-$SO_2$—, or amino-$SO_2$—, and, wherein the phenyl and naphthyl groups are optionally substituted by one to three substituents independently selected from alkyl, cyano, halogeno, alkoxy and trifluoromethyl, or $R^1$ and $R^2$ together with the N atom to which they are attached form an azepane-, a 3,4-dihydro-1H-isoquinoline-, a piperidine-, a pyrrolidine- or a morpholine ring which are optionally substituted with one to three substituents independently selected from alkyl and alkoxy.

Preferred are compounds of formula I, wherein one of $R^1$ and $R^2$ is hydrogen or methyl and the other is independently selected from alkylcarbonyl, cycloalkylcarbonyl, cyanophenyl, alkoxybenyl, cyanophenylcarbonyl, fluorophenylcarbonyl, thiophenylalkyl, pyridinylcarbonyl, furylcarbonyl, alkyl-$SO_2$—, pyridyl-$SO_2$—, pyridinyl and cycloalkylcarbonyl.

A particularly preferred aspect of the present invention are compounds of formula I, wherein one of $R^1$ and $R^2$ is hydrogen or methyl and the other is independently selected from alkylcarbonyl, cycloalkylcarbonyl, cyanophenyl, alkoxybenyl, cyanophenylcarbonyl, fluorophenylcarbonyl, thiophenylalkyl, pyridinylcarbonyl, furylcarbonyl, alkyl-$SO_2$— and pyridyl-$SO_2$—.

Preferred are compounds of formula I, wherein one of $R^1$ and $R^2$ is hydrogen. Particularly preferred are those, wherein one of $R^1$ and $R^2$ is hydrogen and the other is not hydrogen.

Examples of preferred compounds of formula I are:

(R)-N-[4-(2-methoxymethyl-pyrrolidin-1-yl)-2-methyl-quinolin-7-yl]-propionamide;
(2-methoxy-ethyl)-methyl-(2-methyl-4-pyrrolidin-1-yl-quinolin-7-yl)-amine;
(R)-cyclopropylmethyl-[4-(2-methoxymethyl-pyrrolidin-1-yl)-2-methyl-quinolin-7-yl]-amine;
(R,S)-cyclopropylmethyl-[2-methyl-4-(2-methyl-pyrrolidin-1-yl)-quinolin-7-yl]-amine;
(S)-N-[4-(2-hydroxymethyl-pyrrolidin-1-yl)-2-methyl-quinolin-7-yl]-2,2-dimethyl-propionamide;
cyclopropanecarboxylic acid (2-methyl-4-pyrrolidin-1-yl-quinolin-7-yl)-amide;
cyclopropylmethyl-(4-pyrrolidin-1-yl-quinolin-7-yl)-amine;
2,2-dimethyl-N-(2-methyl-4-pyrrolidin-1-yl-quinolin-7-yl)-propionamide;
cyclobutanecarboxylic acid (2-methyl-4-pyrrolidin-1-yl-quinolin-7-yl)-amide;
(2-methyl-4-pyrrolidin-1-yl-quinolin-7-yl)-pyridin-3-yl-amine;
(2-methyl-4-pyrrolidin-1-yl-quinolin-7-yl)-phenyl-amine;
4-(2-methyl-4-pyrrolidin-1-yl-quinolin-7-ylamino)-benzonitrile;

N-(2-methyl-4-pyrrolidin-1-yl-quinolin-7-yl)-propionamide;
3-methyl-N-(2-methyl-4-pyrrolidin-1-yl-quinolin-7-yl)-butyramide;
(2-methoxy-ethyl)-(2-methyl-4-pyrrolidin-1-yl-quinolin-7-yl)-amine;
isobutyl-(2-methyl-4-pyrrolidin-1-yl-quinolin-7-yl)-amine;
furan-2-carboxylic acid (2-methyl-4-pyrrolidin-1-yl-quinolin-7-yl)-amide;
N-(2-methyl-4-pyrrolidin-1-yl-quinolin-7-yl)-nicotinamide;
(2-methyl-4-pyrrolidin-1-yl-quinolin-7-yl)-(2-trifluoromethyl-benzyl)-amine;
(2,3-dimethyl-benzyl)-(2-methyl-4-pyrrolidin-1-yl-quinolin-7-yl)-amine;
[2-(2-chloro-phenyl)-ethyl]-(2-methyl-4-pyrrolidin-1-yl-quinolin-7-yl)-amine;
cyclopropylmethyl-(2-methyl-4-pyrrolidin-1-yl-quinolin-7-yl)-amine;
(2,2-dimethyl-propyl)-(2-methyl-4-pyrrolidin-1-yl-quinolin-7-yl)-amine;
indan-1-yl-(2-methyl-4-pyrrolidin-1-yl-quinolin-7-yl)-amine;
methyl-(2-methyl-4-pyrrolidin-1-yl-quinolin-7-yl)-phenyl-amine;
4-[(2-methyl-4-pyrrolidin-1-yl-quinolin-7-ylamino)-methyl]-benzonitrile;
(4-fluoro-benzyl)-(2-methyl-4-pyrrolidin-1-yl-quinolin-7-yl)-amine;
4-cyano-N-(2-methyl-4-pyrrolidin-1-yl-quinolin-7-yl)-benzamide;
(2-methoxy-benzyl)-(2-methyl-4-pyrrolidin-1-yl-quinolin-7-yl)-amine
(2,6-difluoro-benzyl)-(2-methyl-4-pyrrolidin-1-yl-quinolin-7-yl)-amine;
benzhydryl-(2-methyl-4-pyrrolidin-1-yl-quinolin-7-yl)-amine;
ethyl-(2-methyl-4-pyrrolidin-1-yl-quinolin-7-yl)-pyridin-4-ylmethyl-amine;
furan-2-ylmethyl-(2-methyl-4-pyrrolidin-1-yl-quinolin-7-yl)-amine;
(2-methyl-4-pyrrolidin-1-yl-quinolin-7-yl)-thiophen-2-ylmethyl-amine;
7-azepan-1-yl-2-methyl-4-pyrrolidin-1-yl-quinoline;
2-fluoro-N-(2-methyl-4-pyrrolidin-1-yl-quinolin-7-yl)-benzamide;
4-methoxy-N-(2-methyl-4-pyrrolidin-1-yl-quinolin-7-yl)-benzamide;
4-fluoro-N-(2-methyl-4-pyrrolidin-1-yl-quinolin-7-yl)-benzamide;
N-(2-methyl-4-pyrrolidin-1-yl-quinolin-7-yl)-isonicotinamide;
(4-azepan-1-yl-2-methyl-quinolin-7-yl)-(4-trifluoromethyl-benzyl)-amine;
(2-methyl-benzyl)-(2-methyl-4-pyrrolidin-1-yl-quinolin-7-yl)-amine;
(3,5-dimethyl-benzyl)-(2-methyl-4-pyrrolidin-1-yl-quinolin-7-yl)-amine;
(4-azepan-1-yl-2-methyl-quinolin-7-yl)-pyridin-3-ylmethyl-amine;
(2-methyl-4-pyrrolidin-1-yl-quinolin-7-yl)-naphthalen-1-ylmethyl-amine;
[1-(4-chloro-phenyl)-ethyl]-(2-methyl-4-pyrrolidin-1-yl-quinolin-7-yl)-amine;
N-(2-methyl-4,6-di-pyrrolidin-1-yl-quinolin-7-yl)-acetamide hydrochloride;
2-methyl-4,6-di-pyrrolidin-1-yl-quinolin-7-ylamine; hydrochloride;
(4-methyl-benzyl)-(2-methyl-4-pyrrolidin-1-yl-quinolin-7-yl)-amine;
methyl-(2-methyl-4-pyrrolidin-1-yl-quinolin-7-yl)-pyridin-3-ylmethyl-amine;
(3-methoxy-benzyl)-(2-methyl-4-pyrrolidin-1-yl-quinolin-7-yl)-amine;
(2,4-difluoro-benzyl)-(2-methyl-4-pyrrolidin-1-yl-quinolin-7-yl)-amine;
(4-methoxy-benzyl)-(2-methyl-4-pyrrolidin-1-yl-quinolin-7-yl)-amine;
(2-methyl-4-pyrrolidin-1-yl-quinolin-7-yl)-pyridin-4-ylmethyl-amine;
7-(3,4-dihydro-1H-isoquinolin-2-yl)-2-methyl-4-pyrrolidin-1-yl-quinoline;
(2-methyl-4-pyrrolidin-1-yl-quinolin-7-yl)-(4-trifluoromethyl-benzyl)-amine;
(2-chloro-benzyl)-(2-methyl-4-pyrrolidin-1-yl-quinolin-7-yl)-amine;
(2-methyl-4-pyrrolidin-1-yl-quinolin-7-yl)-pyridin-3-ylmethyl-amine;
(4-chloro-benzyl)-(2-methyl-4-pyrrolidin-1-yl-quinolin-7-yl)-amine;
2-methyl-7-piperidin-1-yl-4-pyrrolidin-1-yl-quinoline;
2-methyl-4,7-di-pyrrolidin-1-yl-quinoline;
2-methyl-7-morpholin-4-yl-4-pyrrolidin-1-yl-quinoline;
(2-methyl-4-pyrrolidin-1-yl-quinolin-7-yl)-(3-methyl-thiophen-2-ylmethyl)-amine;
(S)-N-[4-(2-hydroxymethyl-pyrrolidin-1-yl)-2-methyl-quinolin-7-yl]-nicotinamide;
N-methyl-N-(2-methyl-4-pyrrolidin-1-yl-quinolin-7-yl)-nicotinamide;
(S)-furan-2-carboxylic acid [4-(2-hydroxymethyl-pyrrolidin-1-yl)-2-methyl-quinolin-7-yl]-amide;
N-(2-methyl-4-pyrrolidin-1-yl-quinolin-7-yl)-methanesulfonamide;
4-methyl-N-(2-methyl-4-pyrrolidin-1-yl-quinolin-7-yl)-benzenesulfonamide;
pyridine-3-sulfonic acid (2-methyl-4-pyrrolidin-1-yl-quinolin-7-yl)-amide;
5-chloro-thiophene-2-sulfonic acid (2-methyl-4-pyrrolidin-1-yl-quinolin-7-yl)-amide and
N-methyl-N-(2-methyl-4-pyrrolidin-1-yl-quinolin-7-yl)-benzenesulfonamide.
(2-chloro-pyridin-3-yl)-(2-methyl-4-pyrrolidin-1-yl-quinolin-7-yl)-amine;
(R)-4-[4-(2-methoxymethyl-pyrrolidin-1-yl)-2-methyl-quinolin-7-ylamino]-benzonitrile;
(R)-4-cyano-N-[4-(2-methoxymethyl-pyrrolidin-1-yl)-2-methyl-quinolin-7-yl]-benzamide;
(R)-N-[4-(2-methoxymethyl-pyrrolidin-1-yl)-2-methyl-quinolin-7-yl]-acetamide;
(R)-4-fluoro-N-[4-(2-methoxymethyl-pyrrolidin-1-yl)-2-methyl-quinolin-7-yl]-benzamide;
(S)-4-[4-(2-hydroxymethyl-pyrrolidin-1-yl)-2-methyl-quinolin-7-ylamino]-benzonitrile;
(S)-{1-[2-methyl-7-(pyridin-3-ylamino)-quinolin-4-yl]-pyrrolidin-2-yl}-methanol;
(S)-furan-2-carboxylic acid [4-(2-hydroxymethyl-pyrrolidin-1-yl)-2-methyl-quinolin-7-yl]-amide;
(S)-{1-[7-(2-chloro-pyridin-3-ylamino)-2-methyl-quinolin-4-yl]-pyrrolidin-2-yl}-methanol;
(S)-cyclopropanecarboxylic acid [4-(2-hydroxymethyl-pyrrolidin-1-yl)-2-methyl-quinolin-7-yl]-amide;
(S)-4-cyano-N-[4-(2-hydroxymethyl-pyrrolidin-1-yl)-2-methyl-quinolin-7-yl]-benzamide;
(S)-4-fluoro-N-[4-(2-hydroxymethyl-pyrrolidin-1-yl)-2-methyl-quinolin-7-yl]-benzamide;

(S)-[4-(3-methoxy-pyrrolidin-1-yl)-2-methyl-quinolin-7-yl]-pyridin-3-yl-amine;
(S)-N-[4-(3-methoxy-pyrrolidin-1-yl)-2-methyl-quinolin-7-yl]-nicotinamide;
(S)-N-[4-(3-methoxy-pyrrolidin-1-yl)-2-methyl-quinolin-7-yl]-propionamide;
(S)-4-cyano-N-[4-(3-methoxy-pyrrolidin-1-yl)-2-methyl-quinolin-7-yl]-benzamide;
(S)-cyclopropanecarboxylic acid [4-(3-ethoxy-pyrrolidin-1-yl)-2-methyl-quinolin-7-yl]-amide;
(S)-furan-2-carboxylic acid [4-(3-ethoxy-pyrrolidin-1-yl)-2-methyl-quinolin-7-yl]-amide;
(S)-4-[4-(3-ethoxy-pyrrolidin-1-yl)-2-methyl-quinolin-7-ylamino]-benzonitrile;
(S)-N-[4-(3-ethoxy-pyrrolidin-1-yl)-2-methyl-quinolin-7-yl]-nicotinamide;
(S)-[4-(3-ethoxy-pyrrolidin-1-yl)-2-methyl-quinolin-7-yl]-pyridin-3-yl-amine;
(S)-N-[4-(3-Ethoxy-pyrrolidin-1-yl)-2-methyl-quinolin-7-yl]-propionamide;
(S)-N-[4-(3-ethoxy-pyrrolidin-1-yl)-2-methyl-quinolin-7-yl]-4-fluoro-benzamide;
(S)-4-cyano-N-[4-(3-ethoxy-pyrrolidin-1-yl)-2-methyl-quinolin-7-yl]-benzamide;
(S)-N-[4-(3-ethoxy-pyrrolidin-1-yl)-2-methyl-quinolin-7-yl]-2,2-dimethyl-propionamide;
(S)-2-(4-chloro-phenyl)-N-[4-(3-ethoxy-pyrrolidin-1-yl)-2-methyl-quinolin-7-yl]-acetamide;
(S)-N-[4-(3-ethoxy-pyrrolidin-1-yl)-2-methyl-quinolin-7-yl]-2-pyridin-2-yl-acetamide;
(S)-N-[4-(3-ethoxy-pyrrolidin-1-yl)-2-methyl-quinolin-7-yl]-2-(4-methoxy-phenyl)-acetamide;
(S)-N-[4-(3-ethoxy-pyrrolidin-1-yl)-2-methyl-quinolin-7-yl]-2-(3-trifluoromethyl-phenyl)-acetamide;
(S)-4-[4-(2-methoxy-methyl-pyrrolidin-1-yl)-2-methyl-quinolin-7-ylamino]-benzonitrile;
(S)-(4-fluoro-phenyl)-[4-(2-methoxymethyl-pyrrolidin-1-yl)-2-methyl-quinolin-7-yl]-amine;
(S)-4-(2-methoxymethyl-pyrrolidin-1-yl)-2-methyl-quinolin-7-yl]-pyridin-3-yl-amine;
(S)-cyclopropanecarboxylic acid [4-(2-methoxymethyl-pyrrolidin-1-yl)-2-methyl-quinolin-7-yl]-amide;
(S)-N-[4-(2-methoxymethyl-pyrrolidin-1-yl)-2-methyl-quinolin-7-yl]-2,2-dimethyl-propionamide;
(S)-cyclopropylmethyl-[4-(2-methoxymethyl-pyrrolidin-1-yl)-2-methyl-quinolin-7-yl]-amine;
(S)-N-[4-(2-methoxymethyl-pyrrolidin-1-yl)-2-methyl-quinolin-7-yl]-propionamide;
(S)-4-cyano-N-[4-(2-methoxymethyl-pyrrolidin-1-yl)-2-methyl-quinolin-7-yl]-benzamide;
(S)-[4-(2-ethoxymethyl-pyrrolidin-1-yl)-2-methyl-quinolin-7-yl]-(4-fluoro-phenyl)-amine;
(S)-[4-(2-ethoxymethyl-pyrrolidin-1-yl)-2-methyl-quinolin-7-yl]-pyridin-3-yl-amine;
(S)-furan-2-carboxylic acid [4-(2-ethoxymethyl-pyrrolidin-1-yl)-2-methyl-quinolin-7-yl]-amide;
(R/S)-4-[4-(2-methyl-pyrrolidin-1-yl)-quinolin-7-ylamino]-benzonitrile;
(S)-4-[4-(2-cyclopropylmethoxymethyl-pyrrolidin-1-yl)-2-methyl-quinolin-7-ylamino]-benzonitrile;
(S)-[4-(2-cyclopropylmethoxymethyl-pyrrolidin-1-yl)-2-methyl-quinolin-7-yl]-pyridin-3-yl-amine;
(R)-4-cyano-N-[4-(3-ethoxy-pyrrolidin-1-yl)-2-methyl-quinolin-7-yl]-benzamide;
(S)-N-[4-(3-cyclopropylmethoxy-pyrrolidin-1-yl)-2-methyl-quinolin-7-yl]-nicotinamide; furan-2-carboxylic acid (2,6-dimethyl-4-pyrrolidin-1-yl-quinolin-7-yl)-amide; and
N-(2,6-dimethyl-4-pyrrolidin-1-yl-quinolin-7-yl)-propionamide.

Examples of particularly preferred compounds of formula I are:

cyclopropanecarboxylic acid (2-methyl-4-pyrrolidin-1-yl-quinolin-7-yl)-amide;
2,2-dimethyl-N-(2-methyl-4-pyrrolidin-1-yl-quinolin-7-yl)-propionamide;
4-(2-methyl-4-pyrrolidin-1-yl-quinolin-7-ylamino)-benzonitrile;
3-methyl-N-(2-methyl-4-pyrrolidin-1-yl-quinolin-7-yl)-butyramide;
isobutyl-(2-methyl-4-pyrrolidin-1-yl-quinolin-7-yl)-amine;
N-(2-methyl-4-pyrrolidin-1-yl-quinolin-7-yl)-nicotinamide;
(2,2-dimethyl-propyl)-(2-methyl-4-pyrrolidin-1-yl-quinolin-7-yl)-amine;
4-cyano-N-(2-methyl-4-pyrrolidin-1-yl-quinolin-7-yl)-benzamide;
(2-methoxy-benzyl)-(2-methyl-4-pyrrolidin-1-yl-quinolin-7-yl)-amine;
(2-methyl-4-pyrrolidin-1-yl-quinolin-7-yl)-thiophen-2-ylmethyl-amine;
4-fluoro-N-(2-methyl-4-pyrrolidin-1-yl-quinolin-7-yl)-benzamide;
N-(2-methyl-4-pyrrolidin-1-yl-quinolin-7-yl)-isonicotinamide;
(S)-N-[4-(2-hydroxymethyl-pyrrolidin-1-yl)-2-methyl-quinolin-7-yl]-nicotinamide;
N-methyl-N-(2-methyl-4-pyrrolidin-1-yl-quinolin-7-yl)-nicotinamide;
(S)-furan-2-carboxylic acid [4-(2-hydroxymethyl-pyrrolidin-1-yl)-2-methyl-quinolin-7-yl]-amide;
N-(2-methyl-4-pyrrolidin-1-yl-quinolin-7-yl)-methanesulfonamide;
pyridine-3-sulfonic acid (2-methyl-4-pyrrolidin-1-yl-quinolin-7-yl)-amide;
(R)-4-[4-(2-methoxymethyl-pyrrolidin-1-yl)-2-methyl-quinolin-7-ylamino]-benzonitrile;
(S)-4-[4-(2-hydroxymethyl-pyrrolidin-1-yl)-2-methyl-quinolin-7-ylamino]-benzonitrile;
(S)-[4-(3-methoxy-pyrrolidin-1-yl)-2-methyl-quinolin-7-yl]-pyridin-3-yl-amine;
(S)-cyclopropanecarboxylic acid [4-(3-ethoxy-pyrrolidin-1-yl)-2-methyl-quinolin-7-yl]-amide;
(S)-4-[4-(3-ethoxy-pyrrolidin-1-yl)-2-methyl-quinolin-7-ylamino]-benzonitrile;
(S)-[4-(3-ethoxy-pyrrolidin-1-yl)-2-methyl-quinolin-7-yl]-pyridin-3-yl-amine;
(S)-N-[4-(3-Ethoxy-pyrrolidin-1-yl)-2-methyl-quinolin-7-yl]-propionamide;
(S)-cyclopropanecarboxylic acid [4-(2-methoxymethyl-pyrrolidin-1-yl)-2-methyl-quinolin-7-yl]-amide;
furan-2-carboxylic acid (2,6-dimethyl-4-pyrrolidin-1-yl-quinolin-7-yl)-amide; and
N-(2,6-dimethyl-4-pyrrolidin-1-yl-quinolin-7-yl)-propionamide.

Processes for the manufacture of compounds of formula I are an object of the invention.

The substituents and indices used in the following description of the processes have the significance given above unless indicated to the contrary.

Compounds of general formula I can be obtained according to scheme 1 from compounds of formula Ia (Hal means Cl, Br or I) comprising $R^3$ and $R^4$ substituents and A according to the above definition by an Pd catalysed coupling reaction under Buchwald conditions from the correponding amines or amides sulfonamides with, for example, Pd(OAc)₂ as catalyst, BINAP (2,2 bis(dipenylphosphino)-1,1-binaphthyl) or Xanthphos as chelating phosphine ligand, or with other Palladium catalysts such as SK-CC01-A (commercial from Solvias), and with NaOtBu or cesium carbonate as a base—in a solvent such as toluene or dioxane, and at elevated temperature (S. L. Buchwald in: J Am. Chem. Soc. 1996, p. 10333, Acc. Chem Res. 1998, p 805, Org Lett., 2000, 2, 1104).

Alternatively, the couplings can achieved via an Ullman-type reaction with, for example Cu(I) chloride, or Cu(I) iodide in a solvent such as dioxane or DMF, in analogy to a methods described by J. A. Ragan (Synthesis 1998, p1599) and more recently by S. L. Buchwald (J. Am. Chem. Soc., 2001, 7727).

Scheme 1

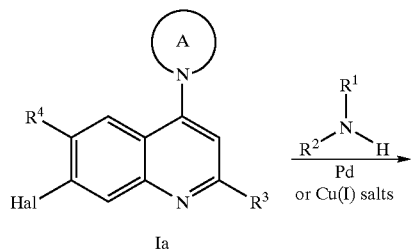

Alternatively, compounds of formula I can be obtained from Ib, according to scheme 2, by an appropriate sequence of alkylation reactions with corresponding alkyl halogenides in the presence of a base such as sodium hydride in THF or DMSO or by using Buchwald-type Pd catalyzed C/N bond formation reactions or Ullaman-type coupling with aryl and heteroaryl amines as discussed above—for the cases were $R^1$,$R^2$ equals aryl and heteroaryl). Compounds with $R^1$, $R^2$ equaling alkylcarbonyl, arylcarbonyl, heterocylycarbonyl aryl-, heteroaryl- or alkyl sulfonyl can prepared from Ib via an acylation (or sulfonation) reaction from corresponding acyl halogenides or sulfonyl chlorides in the presence of a base such as DMAP triethyl amine, and in solvents such as THF or DMF or methylene chloride. Hal in scheme 2 means chloro, bromo or iodo.

Scheme 2

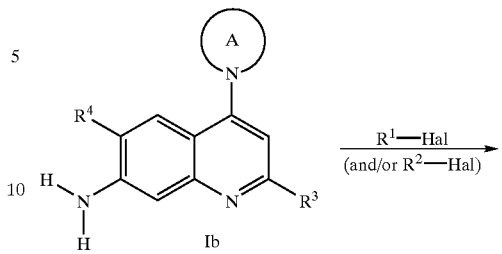

A further alternative consists of having the corresponding substituents already incorporated in the scaffold on preparation of the compounds of formula I according to the schemes shown below.

Compounds with $R^4$ having the meaning as defined above can be prepared from 1c (scheme 3) in a Pd catalyzed Buchwald couplings (from corresponding amines or N-heterocycles), or from $R^{4-}M$ (M means Sn(Bu)₃, or B(OH)₂ or Li and Mg salts) in Stille-, Suzuki- or Negishi-type cross-couplings essentially as known in the literature, or $R_4$ is already incorporated in the scaffold according to the reaction sequences shown below.

Scheme 3

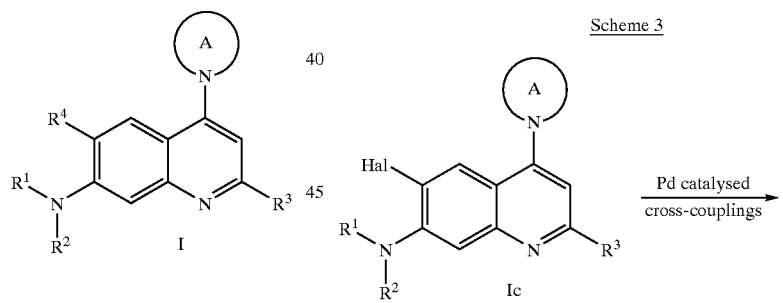

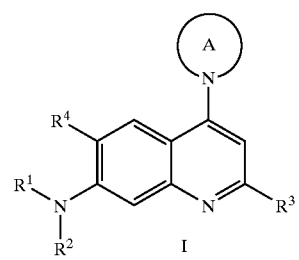

Alternatively, substitutents as $R^4$ (heterocylyl, amino) can be introduced according to scheme 4 on reaction of compounds of formula 1d with an correponding amine or N-heterocyle and in a suitable solvent such as THF or DMSO (Hal means F, Cl, Br or I), or via Pd catalysed bond forming reactions as above to give Ie (Hal means Cl, Br or I). The conversion of 1e to 1b is accomplished by reduction with for example SnCl$_2$ as reducing agent, essentially as known in the literature. An alternative sequence consists of transformation of Id in If by, for example SnCl$_2$ reduction followed by Palladium catalyzed cross-coupling reactions as discussed above.

Scheme 4

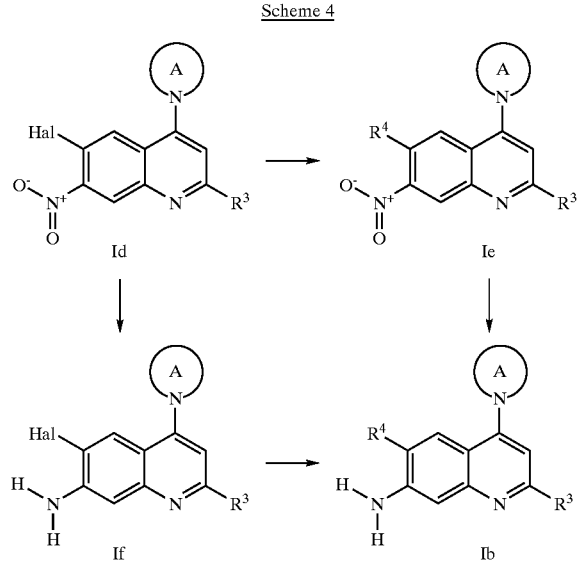

Compounds of general formula Ia-f can be prepared as follows:

The preparation of compounds according to formula Ia1 wherein $R^3$ is hydrogen or alkyl, is achieved is according to scheme 5, starting from appropriate anilines IIIa which are either known in the literature or which can being prepared by standard procedures known in the art. Thus, condensation with corresponding alkoxycarbonyl ketones or aldehydes in the presence of p-toluenesulfonic acid, in refluxing cyclohexane and under capture of water produced during the reaction, the enamine derivatives of general formula IV are obtained. Subsequent ring closure is achieved on heating at 250° C. in a high boiling solvent such as Dowtherm A to give compounds of general formula V. Transformation to the corresponding chloro quinoline derivatives of formula VI is performed on treatment with POCl$_3$ under reflux, a standard method known in the literature. Subsequent reaction with corresponding amines as defined above, either using a large excess of amine without solvent or on reaction with a 2-fold access in a suited solvent such as N-methyl pyrrolidone, xylol, ethanol or THF, optionally in the presence of catalytic amounts of NaI and with pyridine as a base, gives compounds of formula Ia1.

Scheme 5

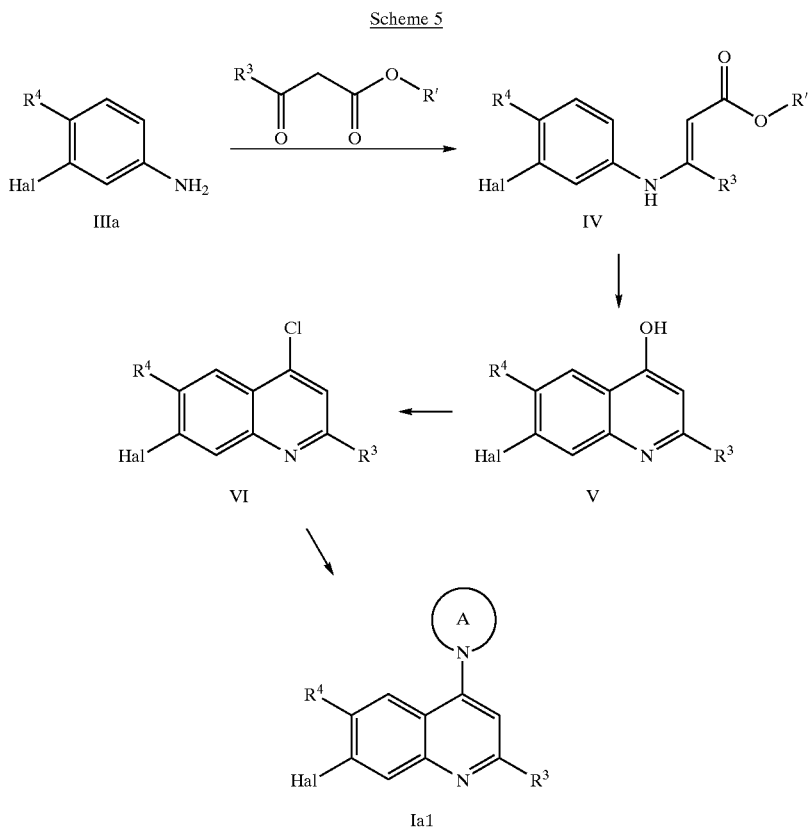

$R^3$ is hydrogen or alkyl;
$R'$ is methyl or ethyl

Compounds Ib1–If1 can be prepared also according to scheme 6 starting from appropriately substitutes anilines of formula IIIb-f with corresponding transformations applied as outlined in Scheme 5.

Scheme 6

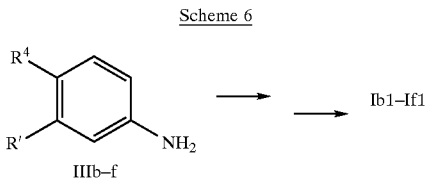

IIIb: R' means $NH_2$; $R^4$ is defined as before;

IIIc: R' means $NR^1R^2$, $R^4$ means Hal;

IIId: R' means $NO_2$, $R^4$ means Hal;

IIIe: R' means $NO_2$, $R^4$ as defined before;

IIIf: R' means $NH_2$, $R^4$ means Hal;

Compounds of formula Ia2, with $R^3$ equaling $NH_2$, alkylamino, dialkylamino or chloro can be prepared according to scheme 7 from anilines of formula IIIa, by condensation with alkyl cyanoacetates, ring closure and subsequent functional group transformations as described above. The corresponding compounds with alkylamino or dialkylamino as $R^3$ can be obtained from, for example, intermediate VIII or Ia2 ($R^3$ means $NH_2$) by selective N-alkylation. Compounds with $R^3$ means Cl can be obtained from Ia2 ($R^3$ means $NH_2$) via diazoniation and Sandmeyer reaction with $CuCl_2$.

Scheme 7

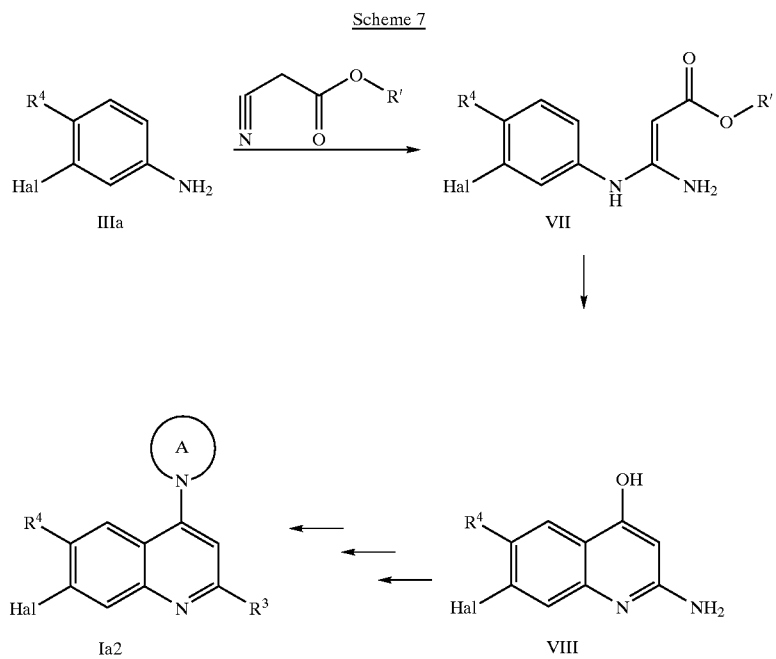

$R^3$ is $NH_2$, alkylamino or dialkylamino;
R' is methyl or ethyl;

In analogy to the sequence described in scheme 7 and starting from the appropriate anilines of formula IIIb-f, there can be obtained the compounds of formula Ib2–If2 ($R^3$ equaling $NH_2$— or alkylamino or dialkylamino or chloro).

A further method to prepare compounds of general formula Ia2, comprises condensation of anilines of formula IIIa with malonic esters to give compounds of formula IX. Subsequent ring closure provides the 2,4-dihydroxyquinolines of general formula X. Subsequent chlorination with $POCl_3$ gives then the 2,4-dichloro-quinolines of formula XI which can be selectively transformed to compounds of type Ia2 by sequential substitution reactions with the corresponding amines in analogy to known reactions in the literature. The compounds Ib2–If2, can be prepared accordingly from IIIb-f as outlined above.

Scheme 8

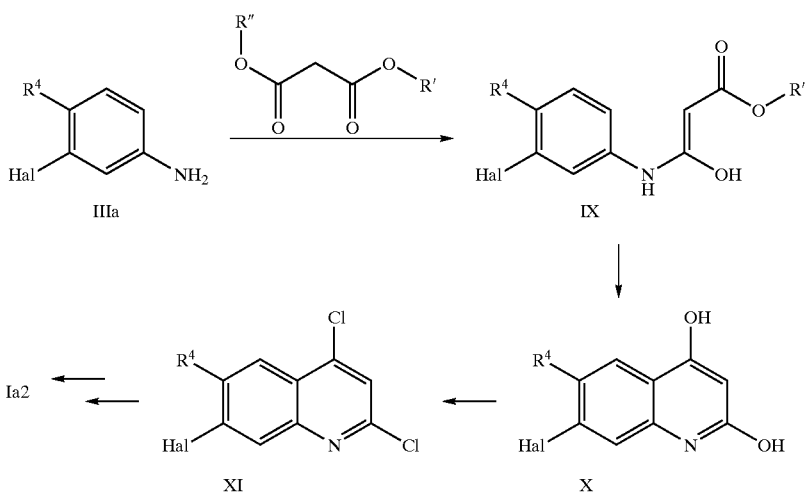

R³ is NH₂, alkylamino, dialkyl amino or chloro
R', R" is methyl or ethyl

Preferred procedures are according to schemes 1, 2, 3 and 5.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid.

The conversion of compounds of formula I into pharmaceutically usable esters or amides can be carried out e.g. by treatment of suited amino or hydroxyl groups present in the molecules with an carboxylic acid such as acetic acid, with a condensating reagent such as benzotriazol-1-yloxytris (dimethylamino)phosphonium hexafluorophosphate (BOP) or N,N-dicylohexylcarbodiimide (DCC) to produce the carboxylic ester or carboxylic amide.

Preferred intermediates are:

7-iodo-2-methyl-4-pyrrolidin-1-yl-quinoline
(R)-7-iodo-4-(2-methoxymethyl-pyrrolidin-1-yl)-2-methyl-quinoline
7-iodo-4-pyrrolidin-1-yl-quinoline
4-azepan-1-yl-7-iodo-2-methyl-quinoline
(S)-[1-(7-iodo-2-methyl-quinolin-4-yl)-pyrrolidin-2-yl]-methanol
(S)-4-(3-ethoxy-pyrrolidin-1-yl)-7-iodo-2-methyl-quinoline hydrochloride
(S)-7-iodo-4-(2-methoxymethyl-pyrrolidin-1-yl)-2-methyl-quinoline
(S)-4-(2-ethoxymethyl-pyrrolidin-1-yl)-7-iodo-2-methyl-quinoline hydrochloride
(S)-4-(2-cyclopropylmethoxymethyl-pyrrolidin-1-yl)-7-iodo-2-methyl-quinoline hydrochloride
(R)-1-(7-iodo-2-methyl-quinolin-4-yl)-pyrrolidin-3-ol
(R)-4-(3-ethoxy-pyrrolidin-1-yl)-7-iodo-2-methyl-quinoline hydrochloride
(S)-1-(7-iodo-2-methyl-quinolin-4-yl)-pyrrolidin-3-ol
(S)-4-(3-cyclopropylmethoxy-pyrrolidin-1-yl)-7-iodo-2-methyl-quinoline
7-Iodo-2,6-dimethyl-4-pyrrolidin-1-yl-quinoline The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions comprising a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

A preferred process for the preparation of a compound according to formula I comprises one of the following reactions:

Reaction of a compound according to formula Ia in the presence of a compound of formula XII in order to obtain a compound of formula I,

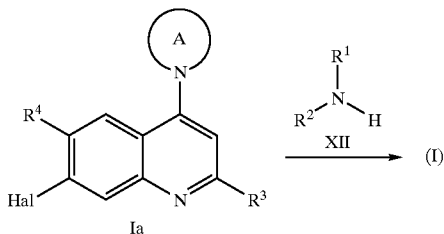

wherein $R^1$ to $R^4$ and A are defined as before and Hal means chloro, bromo or iodo. In a preferred aspect this reaction is performed by an Pd catalysed coupling reaction under Buchwald conditions. Alternatively preferred is the above reaction in the presence of Cu(I) salts, preferably Cu(I) chloride or Cu(I)iodide.

Reaction of a compound according to formula Ib in the presence of one or both compounds of formula $R^1$-Hal and $R^2$-Hal in order to obtain a compound of formula I,

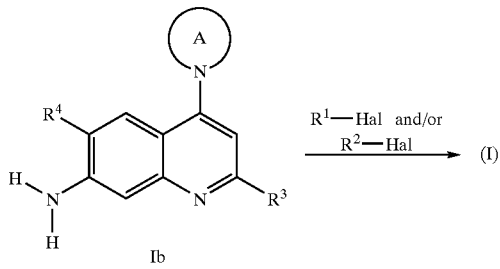

wherein $R^1$ to $R^4$ and A are defined as before and Hal means chloro, bromo or iodo.

Reaction of a compound according to formula Ic in the presence of at least one of the following compounds selected from $R^4$-Hal, $R^4Sn(Bu)_3$, $R^4B(OH)_2$, $LiR^4$ and $HalMgR^4$, preferably $R^4$-Hal, $R^4Sn(Bu)_3$, $R^4B(OH)_2$, in order to obtain a compound of formula I,

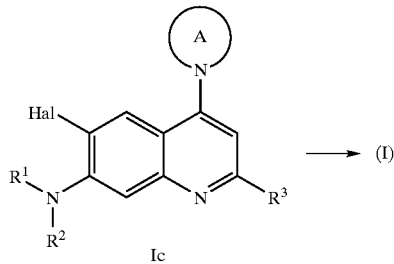

wherein $R^1$ to $R^4$ and A are defined as in claim 1 and Hal means chloro, bromo or iodo.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention is a pharmaceutical composition comprising a compound of formula I described above and a therapeutically inert carrier. Preferred is this composition comprising further a therapeutically effective amount of a lipase inhibitor.

Particularly preferred is the above composition, wherein the lipase inhibitor is orlistat.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Assay Procedures

Cloning of Mouse NPY5 Receptor cDNAs:

The full-length cDNA encoding the mouse NPY5 (mNPY5) receptor was amplified from mouse brain cDNA using specific primers, designed based on the published sequence, and Pfu DNA-Polymerase (Stratagene). The amplification product was subcloned into the mammalian expression vector pcDNA3 using Eco RI and XhoI restriction sites. Positive clones were sequenced and one clone, encoding the published sequence (see Borowsky B., et al., Regul. Pept., 75–76:45–53 (1998)) was selected for generation of stable cell clones.

Stable Transfection:

Human embryonic kidney 293 (HEK293) (ATCC No. CRL-1573) cells were transfected with 10 µg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding:

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 µl 25 mM Hepes buffer (pH 7.4, 2.5 mM $CaCl_2$, 1 mM $MgCl_2$, 1% bovine serum albumine, and 0.01% $NaN_3$ containing 5 µg protein, 100 pM [$^{125}$I]labelled peptide YY (PYY) and 10 µL DMSO containing increasing amounts of unlabelled test compounds. After incubation for 1 h at 22° C., bound and free ligand are separated by filtration over glass fibre filters. Non specific binding is assessed in the presence of 1 µM unlabelled PYY. Specific binding is defined as the difference between total binding and non specific binding. $IC_{50}$ values are defined as the concentration of antagonist that displaces 50% of the binding of [$^{125}$I] labelled neuropeptide Y. It is determined by linear regression analysis after logit/log transformation of the binding data.

Results obtained in the foregoing test using representative compounds of the invention as the test compounds are shown in the following table:

| Compound | $IC_{50}$ |
|---|---|
| Example 2 | 0.7 nM |
| Example 54 | 0.3 nM |

Preferred compounds as described above have $IC_{50}$ values below 1000 nM; more preferred compounds have $IC_{50}$ values below 100 nM, particularly below 10 nM. Most preferred compounds have $IC_{50}$ values below 1 nM. These results have been obtained by using the foregoing test.

The compounds of formula I and their pharmaceutically usable salts, solvates and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts, solvates and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts, solvates and esters can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

A suspension of 1.01 g (3 mmol) of 7-iodo-2-methyl-4-pyrrolidin-1-yl-quinoline, 0.186 g (0.3 mmol) rac BINAP, 33.7 mg (0.15 mmol) of palladium(II)acetate and 0.87 g (9 mmol) of sodium tert-butylate in toluene (25 ml) was treated at RT with 0.427 g (6 mmol) of aminomethyl cyclopropane and then heated to reflux under an argon atmosphere for 20 h. The reaction mixture was then filterd by suction over fiberglass filter paper and the filtrate was partitioned between EtOAc and water. The layers were separated, the organic layer dried over sodium sulphate and concentrated in vacuo. The residue was applied to silica gel column with $CH_2Cl_2$/MeOH/$NH_4OH$ (15:1:0.2) as eluent. Combination of the purified fractions and concentration in vacuo gave 253 mg (30%) of the desired cyclopropylmethyl-(2-methyl-4-pyrrolidin-1-yl-quinolin-7-yl)-amine as light yellow foam. ISP mass spectrum, m/e: 282.2 (M+1 calculated for $C_{18}H_{23}N_3O$: 282).

Preparation of the Starting Material:

A suspension of 2 g (6.59 mmol) of 4-chloro-7-iodo-2-methylquinoline (EP497371) in ethanol (20 ml) was treated successively with 1.28 g (18.0 mmol) of pyrrolidine, pyridine (0.2 ml) and 50 mg (0.3 mmol) of potassium iodide and the resulting mixture was refluxed for 24 h. After concentration in vacuo, the residue was taken up in water (50 ml) and basified to pH 12 by addition of 2 M aq. sodium hydroxide solution. The precipitate was collected by filtration, washed with water (20 ml) and ether (20 ml) and dried to in a high vacuum to afford 1.95 g (87%) of 7-iodo-2-methyl-4-pyrrolidin-1-yl-quinoline as off-white solid, m.p. 99–102° C.

Example 2

In analogy to example 1, on reaction of 7-iodo-2-methyl-4-pyrrolidin-1-yl-quinoline with isobutylamine there was obtained: isobutyl-(2-methyl-4-pyrrolidin-1-yl-quinolin-7-yl)-amine as an off-white white solid. ISP mass spectrum, m/e: 284.2 (M+1 calculated for $C_{18}H_{25}N_3$: 284).

Example 3

In analogy to example 1, on reaction of 7-iodo-2-methyl-4-pyrrolidin-1-yl-quinoline with 2,2-dimetylpropylamine there was obtained: (2,2-dimethyl-propyl)-(2-methyl-4-pyrrolidin-1-yl-quinolin-7-yl)-amine as brown foam. ISP mass spectrum, m/e: 298.4 (M+1 calculated for $C_{19}H_{27}N_3$: 298).

Example 4

In analogy to example 1, on reaction of 7-iodo-2-methyl-4-pyrrolidin-1-yl-quinoline with 2-methoxyetylamine there

Example 5

In analogy to example 1, on reaction of 7-iodo-2-methyl-4-pyrrolidin-1-yl-quinoline with N-(2-methoxyethyl) methylamine there was obtained: (2-methoxy-ethyl)-methyl-(2-methyl-4-pyrrolidin-1-yl-quinolin-7-yl)-amine as amorphous brown solid. ISP mass spectrum, m/e: 300.4 (M+1 calculated for $C_{18}H_{25}N_3O$: 300).

Example 6

In analogy to example 1, on reaction of 7-iodo-2-methyl-4-pyrrolidin-1-yl-quinoline with piperidine there was obtained: 2-methyl-7-piperidin-1-yl-4-pyrrolidin-1-yl-quinoline as brown viscous oil. ISP mass spectrum, m/e: 296.4 (M+1 calculated for $C_{19}H_{25}N_3$: 296).

Example 7

In analogy to example 1, on reaction of 7-iodo-2-methyl-4-pyrrolidin-1-yl-quinoline with pyrrolidine there was obtained: 2-methyl-4,7-di-pyrrolidin-1-yl-quinoline as brown viscous oil. ISP mass spectrum, m/e: 282.2 (M+1 calculated for $C_{18}H_{23}N_3$: 282).

Example 8

In analogy to example 1, on reaction of 7-iodo-2-methyl-4-pyrrolidin-1-yl-quinoline with morpholine there was obtained: 2-Methyl-7-morpholin-4-yl-4-pyrrolidin-1-yl-quinoline a brown viscous oil. ISP mass spectrum, m/e: 298.4 (M+1 calculated for $C_{18}H_{23}N_3O$: 298).

Example 9

In analogy to example 1, on reaction of 7-iodo-2-methyl-4-pyrrolidin-1-yl-quinoline with hexamethylenimine there was obtained: 7-Azepan-1-yl-2-methyl-4-pyrrolidin-1-yl-quinoline as brown viscous oil. ISP mass spectrum, m/e: 310.3 (M+1 calculated for $C_{20}H_{27}N_3$: 310).

Example 10

In analogy to example 1a), on reaction of (R)-7-iodo-4-(2-methoxymethyl-pyrrolidin-1-yl)-2-methyl-quinoline with cyclopropylmethylamine there was obtained: (R)-cyclopropylmethyl-[4-(2-methoxymethyl-pyrrolidin-1-yl)-2-methyl-quinolin-7-yl]-amine an amorphous brown solid. ISP mass spectrum, m/e: 326.4 (M+1 calculated for $C_{20}H_{27}N_3O$: 326).
Preparation of the Starting Material:
In analogy to example 1b), on reaction of 4-chloro-7-iodo-2-methylquinoline with (R)-2-(methoxymethyl)pyrrolidine (commercially available) there was obtained: (R)-7-iodo-4-(2-methoxymethyl-pyrrolidin-1-yl)-2-methyl-quinoline as an off-white solid, m.p. 61–64° C.

Example 11

In analogy to example 1a), on reaction of (R,S)-7-iodo-2-methyl-4-(2-methyl-pyrrolidin-1-yl)-quinoline with cyclopropylmethylamine there was obtained: (R,S)-cyclopropylmethyl-[2-methyl-4-(2-methyl-pyrrolidin-1-yl)-quinolin-7-yl]-amine an amorphous brown solid. ISP mass spectrum, m/e: 396.4 (M+1 calculated for $C_{19}H_{25}N_3$: 296).
Preparation of the Starting Material:
In analogy to example 1b), on reaction of 4-chloro-7-iodo-2-methylquinoline with (R,S)-(2-methyl)pyrrolidine (commercially available) there was obtained: (R,S)-7-iodo-2-methyl-4-(2-methyl-pyrrolidin-1-yl)-quinoline as light brown solid, m.p. 36–40° C.

Example 12

In analogy to example 1a), on reaction 7-iodo-4-pyrrolidin-1-yl-quinoline with cyclopropylmethylamine there was obtained: cyclopropylmethyl-(4-pyrrolidin-1-yl-quinolin-7-yl)-amine a viscous oil. ISP mass spectrum, m/e: 268.4 (M+1 calculated for $C_{17}H_{21}N_3$: 268).
Preparation of the Starting Material
In analogy to example 1b), on reaction of 4-chloro-7-iodo-quinoline (preparation: Surrey at al., JACS, 68, p113, 1946) with pyrrolidine there was obtained: 7-iodo-4-pyrrolidin-1-yl-quinoline as light brown solid. ISP mass spectrum, m/e: 325.2 (M+1 calculated for $C_{13}H_{13}N_2$: 325).

Example 13

In analogy to example 1, on reaction of 7-iodo-2-methyl-4-pyrrolidin-1-yl-quinoline with 3-aminopyridine there was obtained: (2-methyl-4-pyrrolidin-1-yl-quinolin-7-yl)-pyridin-3-yl-amine as brown solid. ISP mass spectrum, m/e: 305.3 (M+1 calculated for $C_{19}H_{20}N_4$: 305).

Example 14

In analogy to example 1, on reaction of 7-iodo-2-methyl-4-pyrrolidin-1-yl-quinoline with aniline there was obtained: (2-methyl-4-pyrrolidin-1-yl-quinolin-7-yl)-phenyl-3-yl-amine as brown solid. ISP mass spectrum, m/e: 304.3 (M+1 calculated for $C_{20}H_{21}N_3$: 304).

Example 15

In analogy to example 1, on reaction of 7-iodo-2-methyl-4-pyrrolidin-1-yl-quinoline with 4-aminobenzonitrile there was obtained: 4-(2-methyl-4-pyrrolidin-1-yl-quinolin-7-ylamino)-benzonitrile as light brown solid. ISP mass spectrum, m/e: 329.4 (M+1 calculated for $C_{21}H_{20}N_4$: 329).

Example 16

In analogy to example 1, on reaction of 7-iodo-2-methyl-4-pyrrolidin-1-yl-quinoline with 2-trifluorometyl-benzylamine there was obtained: (2-methyl-4-pyrrolidin-1-yl-quinolin-7-yl)-(2-trifluoromethyl-benzyl)-amine as light brown foam. ISP mass spectrum, m/e: 386.3 (M+1 calculated for $C_{22}H_{22}F_3N_3$: 386).

Example 17

In analogy to example 1, on reaction of 7-iodo-2-methyl-4-pyrrolidin-1-yl-quinoline with 2,3-dimethylbenzylamine there was obtained: (2,3-dimethyl-benzyl)-(2-methyl-4-pyrrolidin-1-yl-quinolin-7-yl)-amine as light brown foam. ISP mass spectrum, m/e: 346.4 (M+1 calculated for $C_{23}H_{27}F_3N_3$: 346).

Example 18

In analogy to example 1, on reaction of 7-iodo-2-methyl-4-pyrrolidin-1-yl-quinoline with 4-cyano-benzylamine there was obtained: 4-[(2-methyl-4-pyrrolidin-1-yl-quinolin-7-ylamino)-methyl]-benzonitrile as light brown amorphous solid. ISP mass spectrum, m/e: 343.3 (M+1 calculated for $C_{22}H_{22}N_4$: 343).

Example 19

In analogy to example 1, on reaction of 7-iodo-2-methyl-4-pyrrolidin-1-yl-quinoline with 4-fluoro-benzylamine there was obtained: (4-fluoro-benzyl)-(2-methyl-4-pyrrolidin-1-yl-quinolin-7-yl)-amine as light brown solid. ISP mass spectrum, m/e: 336.2 (M+1 calculated for $C_{21}H_{22}F_4N_3$: 335).

Example 20

In analogy to example 1, on reaction of 7-iodo-2-methyl-4-pyrrolidin-1-yl-quinoline with 2-methoxy-benzylamine there was obtained: (2-methoxy-benzyl)-(2-methyl-4-pyrrolidin-1-yl-quinolin-7-yl)-amine as brown solid. ISP mass spectrum, m/e: 348.5 (M+1 calculated for $C_{22}H_{25}N_3O$: 348).

Example 21

In analogy to example 1, on reaction of 7-iodo-2-methyl-4-pyrrolidin-1-yl-quinoline with 2,2-difluorobenzylamine there was obtained: (2,6-Difluoro-benzyl)-(2-methyl-4-pyrrolidin-1-yl-quinolin-7-yl)-amine as light brown solid. ISP mass spectrum, m/e 354.3 (M+1 calculated for $C_{21}H_{21}F_2N_3$: 354).

Example 22

In analogy to example 1, on reaction of 7-iodo-2-methyl-4-pyrrolidin-1-yl-quinoline with benzhydrylamine there was obtained: benzhydryl-(2-methyl-4-pyrrolidin-1-yl-quinolin-7-yl)-amine as yellow oil. ISP mass spectrum, m/e: 394.4 (M+1 calculated for $C_{27}H_{27}N_3$: 394).

Example 23

In analogy to example 1, on reaction of 7-iodo-2-methyl-4-pyrrolidin-1-yl-quinoline with furfurylamine there was obtained: furan-2-ylmethyl-(2-methyl-4-pyrrolidin-1-yl-quinolin-7-yl)-amine as brown oil. ISP mass spectrum, m/e: 308.3 (M+1 calculated for $C_{19}H_{21}N_3O$: 308).

Example 24

In analogy to example 1, on reaction of 7-iodo-2-methyl-4-pyrrolidin-1-yl-quinoline with 2-thiophenemethylamine there was obtained: (2-methyl-4-pyrrolidin-1-yl-quinolin-7-yl)-thiophen-2-ylmethyl-amine as brown oil. ISP mass spectrum, m/e: 324.3 (M+1 calculated for $C_{19}H_{21}N_3S$: 324).

Example 25

In analogy to example 1a), on reaction of 4-azepan-1-yl-7-iodo-2-methyl-quinoline with 4-trifluoromethylbenzylamine there was obtained (4-azepan-1-yl-2-methyl-quinolin-7-yl)-(4-trifluoromethyl-benzyl)-amine a light brown solid. ISP mass spectrum, m/e: 414.3 (M+1 calculated for $C_{24}H_{26}F_3N_3$: 414).
Preparation of the Starting Material:
In analogy to example 1b), on reaction of 4-chloro-7-iodo-2-methylquinoline with hexamethleneimine there was obtained: 4-azepan-1-yl-7-iodo-2-methyl-quinoline as an off-white solid, m.p. 90–93° C.

Example 26

In analogy to example 1, on reaction of 7-iodo-2-methyl-4-pyrrolidin-1-yl-quinoline with 2-methylbenzylamine there was obtained: (2-methyl-benzyl)-(2-methyl-4-pyrrolidin-1-yl-quinolin-7-yl)-amine as yellow solid. ISP mass spectrum, m/e: 332.3 (M+1 calculated for $C_{22}H_{25}N_3$: 332).

Example 27

In analogy to example 1, on reaction of 7-iodo-2-methyl-4-pyrrolidin-1-yl-quinoline with 3,5-dimethylbenzylamine there was obtained: (3,5-Dimethyl-benzyl)-(2-methyl-4-pyrrolidin-1-yl-quinolin-7-yl)-amine as yellow solid. ISP mass spectrum, m/e: 346.4 (M+1 calculated for $C_{23}H_{27}N_3$: 346).

Example 28

In analogy to example 1, on reaction of 4-azepan-1-yl-7-iodo-2-methyl-quinoline, product of example 25b), with 3-(aminometyl)pyridine there was obtained: (4-azepan-1-yl-2-methyl-quinolin-7-yl)-pyridin-3-ylmethyl-amine as brown viscous oil. ISP mass spectrum, m/e: 347.5 (M+1 calculated for $C_{22}H_{26}N_4$: 347).

Example 29

In analogy to example 1, on reaction of 7-iodo-2-methyl-4-pyrrolidin-1-yl-quinoline with 1-naphthalenemetylamine there was obtained: (2-methyl-4-pyrrolidin-1-yl-quinolin-7-yl)-naphthalen-1-ylmethyl-amine as yellow solid. ISP mass spectrum, m/e: 368.3 (M+1 calculated for $C_{25}H_{25}N_3$: 368).

Example 30

In analogy to example 1, on reaction of 7-iodo-2-methyl-4-pyrrolidin-1-yl-quinoline with (R,S)-1-(4-chlorophenyl)-ethylamine there was obtained (R,S)-[1-(4-chloro-phenyl)-ethyl]-(2-methyl-4-pyrrolidin-1-yl-quinolin-7-yl)-amine as yellow solid. ISP mass spectrum, m/e: 366.2 (M+1 calculated for $C_{22}H_{24}ClN_3$: 366).

Example 31

In analogy to example 1, on reaction of 7-iodo-2-methyl-4-pyrrolidin-1-yl-quinoline with 4-methylbenzylamine there was obtained: (4-methyl-benzyl)-(2-methyl-4-pyrrolidin-1-yl-quinolin-7-yl)-amine as light brown solid. ISP mass spectrum, m/e: 332.3 (M+1 calculated for $C_{22}H_{25}N_3$: 332).

Example 32

In analogy to example 1, on reaction of 7-iodo-2-methyl-4-pyrrolidin-1-yl-quinoline with 3-methoxylbenzylamine there was obtained: (3-methoxy-benzyl)-(2-methyl-4-pyrrolidin-1-yl-quinolin-7-yl)-amine as light brown solid. ISP mass spectrum, m/e: 348.4 (M+1 calculated for $C_{22}H_{25}N_3O$: 348).

Example 33

In analogy to example 1, on reaction of 7-iodo-2-methyl-4-pyrrolidin-1-yl-quinoline with 2,4-difluoro-benzylamine there was obtained: (2,4-difluoro-benzyl)-(2-methyl-4-pyrrolidin-1-yl-quinolin-7-yl)-amine as brown solid. ISP mass spectrum, m/e: 354.3 (M+1 calculated for $C_{21}H_{21}F_2N_3$: 354).

Example 34

In analogy to example 1, on reaction of 7-iodo-2-methyl-4-pyrrolidin-1-yl-quinoline with 4-methoxy-benzylamine there was obtained: (4-methoxy-benzyl)-(2-methyl-4-pyrrolidin-1-yl-quinolin-7-yl)-amine as yellow solid. ISP mass spectrum, m/e: 348.4 (M+1 calculated for $C_{22}H_{25}N_3O$: 348).

Example 35

In analogy to example 1, on reaction of 7-iodo-2-methyl-4-pyrrolidin-1-yl-quinoline with 4-(aminomethyl)-pyridine there was obtained: (2-methyl-4-pyrrolidin-1-yl-quinolin-7-

Example 36

In analogy to example 1, on reaction of 7-iodo-2-methyl-4-pyrrolidin-1-yl-quinoline with 4-(trifluoromethyl)-benzylamine there was obtained: (2-methyl-4-pyrrolidin-1-yl-quinolin-7-yl)-(4-trifluoromethyl-benzyl)-amine as yellow solid. ISP mass spectrum, m/e: 386.3 (M+1 calculated for $C_{22}H_{22}F_3N_3$: 386).

Example 37

In analogy to example 1, on reaction of 7-iodo-2-methyl-4-pyrrolidin-1-yl-quinoline with 2-chloro-benzylamine there was obtained: (2-chloro-benzyl)-(2-methyl-4-pyrrolidin-1-yl-quinolin-7-yl)-amine as light brown solid. ISP mass spectrum, m/e: 352.3 (M+1 calculated for $C_{21}H_{22}ClN_3$: 352).

Example 38

In analogy to example 1, on reaction of 7-iodo-2-methyl-4-pyrrolidin-1-yl-quinoline with 3-(aminomethyl)-pyridine there was obtained: (2-methyl-4-pyrrolidin-1-yl-quinolin-7-yl)-pyridin-3-ylmethyl-amine as light brown solid. ISP mass spectrum, m/e: 319.4 (M+1 calculated for $C_{20}H_{22}N_4$: 319).

Example 39

In analogy to example 1, on reaction of 7-iodo-2-methyl-4-pyrrolidin-1-yl-quinoline with 4-chloro-benzylamine there was obtained: (4-chloro-benzyl)-(2-methyl-4-pyrrolidin-1-yl-quinolin-7-yl)-amine as light brown solid. ISP mass spectrum, m/e: 352, 3 (M+1 calculated for $C_{21}H_{22}ClN_3$: 352).

Example 40

In analogy to example 1, on reaction of 7-iodo-2-methyl-4-pyrrolidin-1-yl-quinoline with 1-aminoindane there was obtained: indan-1-yl-(2-methyl-4-pyrrolidin-1-yl-quinolin-7-yl)-amine as brown foam. ISP mass spectrum, m/e: 344.4 (M+1 calculated for $C_{23}H_{25}N_3$: 344).

Example 41

In analogy to example 1, on reaction of 7-iodo-2-methyl-4-pyrrolidin-1-yl-quinoline with N-metylaniline there was obtained: methyl-(2-methyl-4-pyrrolidin-1-yl-quinolin-7-yl)-phenyl-amine as light brown foam. ISP mass spectrum, m/e: 318.3 (M+1 calculated for $C_{21}H_{23}N_3$: 318).

Example 42

In analogy to example 1, on reaction of 7-iodo-2-methyl-4-pyrrolidin-1-yl-quinoline with 4-(etylaminomethyl)-pyridine there was obtained: ethyl-(2-methyl-4-pyrrolidin-1-yl-quinolin-7-yl)-pyridin-4-ylmethyl-amine as brown viscous oil. ISP mass spectrum, m/e: 347.4 (M+1 calculated for $C_{22}H_{26}N_4$: 347).

Example 43

In analogy to example 1, on reaction of 7-iodo-2-methyl-4-pyrrolidin-1-yl-quinoline with 3-(metylaminomethyl)-pyridine there was obtained: methyl-(2-methyl-4-pyrrolidin-1-yl-quinolin-7-yl)-pyridin-3-ylmethyl-amine as light brown viscous oil. ISP mass spectrum, m/e: 333.3 (M+1 calculated for $C_{21}H_{24}N_4$: 333).

Example 44

In analogy to example 1, on reaction of 7-iodo-2-methyl-4-pyrrolidin-1-yl-quinoline with 1,2,3,4-tetrahydroisiquinoline there was obtained: 7-(3,4-dihydro-1H-isoquinolin-2-yl)-2-methyl-4-pyrrolidin-1-yl-quinoline as light brown viscous oil. ISP mass spectrum, m/e: 344.4 (M+1 calculated for $C_{23}H_{25}N_3$: 344).

Example 45

In analogy to example 1, on reaction of 7-iodo-2-methyl-4-pyrrolidin-1-yl-quinoline with 2-(2-chlorophenyl)-ethylamine there was obtained [2-(2-Chloro-phenyl)-ethyl]-(2-methyl-4-pyrrolidin-1-yl-quinolin-7-yl)-amine as light brown foam. ISP mass spectrum, m/e: 366.2 (M+1 calculated for $C_{22}H_{24}ClN_3$: 366).

Example 46

In analogy to example 1, on reaction of 7-iodo-2-methyl-4-pyrrolidin-1-yl-quinoline with 3-metylthiophene-2-metylamine there was obtained (2-methyl-4-pyrrolidin-1-yl-quinolin-7-yl)-(3-methyl-thiophen-2-ylmethyl)-amine as yellow foam. ISP mass spectrum, m/e: 338.3 (M+1 calculated for $C_{20}H_{23}N_3S$: 338).

Example 47

A suspension of 0.338 mg (1 mmol) of 7-iodo-2-methyl-4-pyrrolidin-1-yl-quinoline, 0.81 g (8 mmol) of trimethylacetamide, 0.414 g (3 mmol) of potassium carbonate (water free) and 20 mg (0.1 mmol) of copper (I) iodide in DMF (10 ml) was heated at 150° C. (oil bath temperature) under an argon atmosphere for 20 h. The reaction mixture was partitioned between EtOAc and water, the layers were separated, the organic layer washed twice with water dried over sodium sulphate and concentrated in vacuo. The residue was applied to silica gel column with $CH_2Cl_2$/MeOH/$NH_4OH$ (20:1:0.2) as eluent. Combination of the purified fractions and concentration in vacuo gave 175 mg (50.4%) of the desired 2,2-dimethyl-N-(2-methyl-4-pyrrolidin-1-yl-quinolin-7-yl)-propionamide as light brown solid. ISP mass spectrum, m/e: 312.3 (M+1 calculated for $C_{19}H_{25}N_3O$: 312).

Example 48

In analogy to example 47, on reaction of 7-iodo-2-methyl-4-pyrrolidin-1-yl-quinoline with cyclobutanecarboxamide there was obtained: cyclobutanecarboxylic acid (2-methyl-4-pyrrolidin-1-yl-quinolin-7-yl)-amide as light yellow solid. ISP mass spectrum, m/e: 310.3 (M+1 calculated for $C_{19}H_{23}N_3O$: 310).

Example 49

In analogy to example 47, on reaction of 7-iodo-2-methyl-4-pyrrolidin-1-yl-quinoline with cyclopropanecarboxamide there was obtained: cyclopropanecarboxylic acid (2-methyl-4-pyrrolidin-1-yl-quinolin-7-yl)-amide as light yellow solid. ISP mass spectrum, m/e: 296.4 (M+1 calculated for $C_{18}H21N_3O$: 296).

Example 50

In analogy to example 47, on reaction of (R)-7-iodo-4-(2-methoxymethyl-pyrrolidin-1-yl)-2-methyl-quinoline product of example 10b), with propionamide there was obtained: (R)-N-[4-(2-methoxymethyl-pyrrolidin-1-yl)-2-methyl-quinolin-7-yl]-propionamide as brown solid. ISP mass spectrum, m/e: 328.4 (M+1 calculated for $C_{19}H_{25}N_3O_2$: 328).

Example 51

In analogy to example 47, on reaction of 7-iodo-2-methyl-4-pyrrolidin-1-yl-quinoline with propionamide there was obtained: N-(2-methyl-4-pyrrolidin-1-yl-quinolin-7-yl)-propionamide as brown viscous oil. ISP mass spectrum, m/e: 284.2 (M−1 calculated for $C_{17}H_{21}N_3O$: 284).

Example 52

In analogy to example 47, on reaction of 7-iodo-2-methyl-4-pyrrolidin-1-yl-quinoline with isovaleramide there was obtained: 3-methyl-N-(2-methyl-4-pyrrolidin-1-yl-quinolin-7-yl)-butyramide as crystalline white yellow solid. ISP mass spectrum, m/e: 312.3 (M+1 calculated for $C_{19}H_{25}N_3O$: 312).

Example 53

In analogy to example 47, on reaction of (S)-[1-(7-iodo-2-methyl-quinolin-4-yl)-pyrrolidin-2-yl]-methanol with trimethylacetamide there was obtained (S)-N-[4-(2-hydroxymethyl-pyrrolidin-1-yl)-2-methyl-quinolin-7-yl]-2,2-dimethyl-propionamide as amorphous white yellow solid. ISP mass spectrum, m/e: 342.3 (M+1 calculated for $C_{20}H_{27}N_3O_2$: 342).
Preparation of the Starting Material
A solution of 3.5 g (11.5 mmol) of 4-chloro-7-iodo-2-methylquinoline and 2.92 g (28.8 mmol) of (S)-2-(hydroxymethyl)pyrrolidine in 1-methyl-2-pyrrolidone (50 ml) was heated at 100° C. (oil bath temperature) for 24 h under an argon athmosphere. In order to complete the reaction, 2.2 ml of (S)-2-(hydroxymethyl)pyrrolidine were added and the solution was heated at 100° C. for further 24 h under argon. The solution was then concentrated in a vacuo (4 mbar) at 100° C. The residue was applied to silica gel column with $CH_2Cl_2$/MeOH/$NH_4OH$ (95:5:0.2) as eluent. Combination of the purified fractions and concentration in vacuo gave 2.7 g (64%) of the desired (S)-[1-(7-iodo-2-methyl-quinolin-4-yl)-pyrrolidin-2-yl]-methanol as light brown solid. ISP mass spectrum, m/e: 369.1 (M+1 calculated for $C_{15}H_{17}IN_2O$: 369).

Example 54

In analogy to example 47, on reaction of 7-iodo-2-methyl-4-pyrrolidin-1-yl-quinoline with 2-furamide there was obtained: furan-2-carboxylic acid (2-methyl-4-pyrrolidin-1-yl-quinolin-7-yl)-amide as light yellow solid. ISP mass spectrum, m/e: 322.3 (M+1 calculated for $C_{19}H_{19}N_3O_2$: 322).

Example 55

In analogy to example 47, on reaction of 7-iodo-2-methyl-4-pyrrolidin-1-yl-quinoline with nicotinamide there was obtained: N-(2-methyl-4-pyrrolidin-1-yl-quinolin-7-yl)-nicotinamide as light yellow solid. ISP mass spectrum, m/e: 333.3 (M+1 calculated for $C_{20}H_{20}N_4O$: 333).

Example 56

In analogy to example 47, on reaction of 7-iodo-2-methyl-4-pyrrolidin-1-yl-quinoline with 4-cyanobenzamide there was obtained: 4-cyano-N-(2-methyl-4-pyrrolidin-1-yl-quinolin-7-yl)-benzamide as light brown solid. ISP mass spectrum, m/e: 357.3 (M+1 calculated for $C_{22}H_{20}N_4O$: 357).

Example 57

In analogy to example 47, on reaction of 7-iodo-2-methyl-4-pyrrolidin-1-yl-quinoline with 2-fluorobenzamide there was obtained: 2-fluoro-N-(2-methyl-4-pyrrolidin-1-yl-quinolin-7-yl)-benzamide as light yellow solid. ISP mass spectrum, m/e: 350.3 (M+1 calculated for $C_{21}H_{20}FN_3O$: 350).

Example 58

In analogy to example 47, on reaction of 7-iodo-2-methyl-4-pyrrolidin-1-yl-quinoline with 4-methoxybenzamide there was obtained: 4-methoxy-N-(2-methyl-4-pyrrolidin-1-yl-quinolin-7-yl)-benzamide as light brown solid. ISP mass spectrum, m/e: 362.4 (M+1 calculated for $C_{22}H_{23}N_3O_2$: 362).

Example 59

In analogy to example 47, on reaction of 7-iodo-2-methyl-4-pyrrolidin-1-yl-quinoline with 4-fluorobenzamide there was obtained: 4-fluoro-N-(2-methyl-4-pyrrolidin-1-yl-quinolin-7-yl)-benzamide as light brown solid. ISP mass spectrum, m/e: 350.3 (M+1 calculated for $C_{21}H_{20}FN_3O$: 350).

Example 60

In analogy to example 47, on reaction of 7-iodo-2-methyl-4-pyrrolidin-1-yl-quinoline with isonicotinamide there was obtained: N-(2-methyl-4-pyrrolidin-1-yl-quinolin-7-yl)-isonicotinamide as light brown solid. ISP mass spectrum, m/e: 333.3 (M+1 calculated for $C_{20}H_{20}N_4O$: 333).

Example 61

In analogy to example 47, on reaction of (S)-[1-(7-iodo-2-methyl-quinolin-4-yl)-pyrrolidin-2-yl]-methanol, product of example 53b), with nicotinamide there was obtained: (S)-N-[4-(2-hydroxymethyl-pyrrolidin-1-yl)-2-methyl-quinolin-7-yl]-nicotinamide as off-white solid solid. ISP mass spectrum, m/e: 363.3 (M+1 calculated for $C_{21}H_{22}N_4O_2$: 363).

Example 62

In analogy to example 1, on reaction of 7-iodo-2-methyl-4-pyrrolidin-1-yl-quinoline with N-metylnicotinamide, with Xantphos as phosphine (instead of rac BINAP), Cesium carbonate as base (instead of sodium tert-butylate), in 1,4-dioxane as solvent (general procedure: Buchwald et al: Org. Lett., 2000, 2, 1104) there was obtained: N-Methyl-N-(2-methyl-4-pyrrolidin-1-yl-quinolin-7-yl)-nicotinamide as yellow solid. ISP mass spectrum, m/e: 347.4 (M+1 calculated for $C_{21}H_{22}N_4O$: 347).

Example 63

In analogy to example 47, on reaction of (S)-[1-(7-iodo-2-methyl-quinolin-4-yl)-pyrrolidin-2-yl]-methanol, product of example 53b), with furylamide there was obtained: (S)-furan-2-carboxylic acid [4-(2-hydroxymethyl-pyrrolidin-1-yl)-2-methyl-quinolin-7-yl]-amide as light yellow. ISP mass spectrum, m/e: 352.4 (M+1 calculated for $C_{20}H_{21}N_3O_3$: 352).

Example 64

In a dried reaction flask flushed with argon a suspension of 169 mg (0.5 mmol) 7-iodo-2-methyl-4-pyrrolidin-1-yl-quinoline and 57 mg (0.6 mmol) of methanesulfonamide, 325 mg (1 mmol) of cesium carbonate, 1.9 mg (0.01 mmol) copper (I) iodide in 1,4-dioxane was treated at RT with 5.7 mg (0.05 mmol) of trans-diaminocyclohexane and the mixture was heated at 110° C. (oil bath temperature) for 48 h under an argon atmosphere (for the gerneal method: Buchwald: J. Am. Chem. Soc., p7727, 2001). The reaction mixture was then cooled to RT, diluted with methylene chloride and filtered. The filtrate was concentrated in a vacuo, the residue was applied to silica gel column with $CH_2Cl_2/MeOH/NH_4OH$ (9:1:0.5) as eluent. Combination of the purified fractions and concentration in vacuo gave 29 mg (25.5%) of the desired N-(2-methyl-4-pyrrolidin-1-yl-quinolin-7-yl)-methanesulfonamide which was re-crystallized from methylene chloride: light brown solid. ISP mass spectrum, m/e: 306.3 (M+1 calculated for $C_{15}H_{19}IN_3O_2S$: 306).

Example 65

In analogy to example 64, on reaction of 7-iodo-2-methyl-4-pyrrolidin-1-yl-quinoline with (4-methylphenyl)-sulfonamide there was obtained: 4-methyl-N-(2-methyl-4-pyrrolidin-1-yl-quinolin-7-yl)-benzenesulfonamide as off-white solid. ISP mass spectrum, m/e: 382.4 (M+1 calculated for $C_{21}H_{23}N_3O_3S$: 382).

Example 66

In analogy to example 64, on reaction of 7-iodo-2-methyl-4-pyrrolidin-1-yl-quinoline with pyridyl-3-sulfonamide there was obtained: pyridine-3-sulfonic acid (2-methyl-4-pyrrolidin-1-yl-quinolin-7-yl)-amide as off-white solid. ISN mass spectrum, m/e: 367.1 (M−1 calculated for $C_{19}H_{20}N_4O_2S$: 367).

Example 67

In analogy to example 64, on reaction of 7-iodo-2-methyl-4-pyrrolidin-1-yl-quinoline with 2-chloro-thiophene-2-sulfonamide there was obtained: 5-chloro-thiophene-2-sulfonic acid (2-methyl-4-pyrrolidin-1-yl-quinolin-7-yl)-amide as off-white solid. ISN mass spectrum, m/e: 406.3 (M−1 calculated for $C_{18}H_{18}ClN_3O_2S_2$: 406)

Example 68

In analogy to example 64, on reaction of 7-iodo-2-methyl-4-pyrrolidin-1-yl-quinoline with N-metylbenzenesulfonamide there was obtained: N-methyl-N-(2-methyl-4-pyrrolidin-1-yl-quinolin-7-yl)-benzenesulfonamide as off-white solid. ISP mass spectrum, m/e: 382.4 (M+1 calculated for $C_{21}H_{23}N_3O_2S$: 382).

Example 69

A solution 0.1 g (0.27 mmol of 2-methyl-4,6-di-pyrrolidin-1-yl-quinolin-7-ylamine hydrochloride (×1.58 HCl), product of example 70 in acetic acid (0.22 ml) was treated with 0.1 ml (1.08 mmol) of acetic anhydride and then stirred at RT for 19 h. The reaction mixture was concentrated in vacuo, brought to pH 9 with conc. ammonia and then twice extacted with $CH_2CL_2$. The organic phase was washed with water saturated with brine and dried over magnesium sulfate. The solvent was removed in vacuo, the residue triturated with ether (10 ml) and treated tropwise with 0.3 ml of 3 N HCL in MeOH. The brown crystalline solid obtained was filtered off by suction and dried in a high vacuum to give 58.7 mg (89%) of N-(2-methyl-4,6-di-pyrrolidin-1-yl-quinolin-7-yl)-acetamide hydrochloride as a brown solid. ISP mass spectrum, m/e: 339.3 (M+1 calculated for $C_{20}H_{27}N_4O$: 339).

Example 70

A suspension of 0.28 g (0.86 mmol) of 2-methyl-7-nitro-4,6-di-pyrrolidin-1-yl-quinoline in MeOH (10 ml) is treated with 60 mg of Pd/C (10%) and then hydrogenated under an $H_2$ atmosphere for 2 h at RT until completion of the reaction. The catalyst was filtered off, the filtrate concentrated in vacuo. The residue was triturated with ether (15 ml) and treated tropwise with 1 ml of 3 N HCL in MeOH to give 209 mg (97.4%) of 2-methyl-4,6-di-pyrrolidin-1-yl-quinolin-7-ylamine hydrochloride(×1.58 HCl), as light brown solid. ISP mass spectrum, m/e: 297.4 (M+1 calculated for $C_{18}H_{24}N_4$: 297).

Preparation of the Starting Material:

20 g (156 mmol) of 4-fluor-3-nitro-aniline, 18.9 ml (134 mmol) of ethyl acetoacetate in cyclohexene (35 ml) were treated with p-toluene sulfonic acid monohydrate (0.24 g) and heated for 9 h at reflux under a water separator funnel. The solvent was removed in vacuo, the residue applied to silica gel column with AcOEt/n-hexane (1:1)) as eluent. Combination of the purified fractions and concentration in vacuo gave 4.3 g (12.5%) of the 3-(4-fluoro-3-nitro-phenylamino)-but-2-enoic acid ethyl ester as yellow crystals. ISN mass spectrum, m/e: 267.2 (M−1 calculated for $C_{12}H_{13}FN_2O_4$: 267).

A solution of 3.6 g (13.42 mmol) of 3-(4-fluoro-3-nitro-phenylamino)-but-2-enoic acid ethyl ester in Dowtherm A (10 ml) was added dropwise to 56 ml of Dowtherm A heated at 250° C. Heating was continued for 15 minutes than the suspension was cooled to RT, heptane was added the precipitate collected by filtration, washed with heptane and ether and then dried in a high vacuum to give 1.9 g of ring-closed material light-brown solid as a mixture of two regioismers isomers containing 1.26 g of the desired 6-fluoro-2-methyl-7-nitro-quinolin-4-ol. EI mass spectrum, m/e: 222.2 (M calculated for $C_{10}H_7N_2O_3$: 222). Material was used in the next step without further purification.

Above material (2.05 g) was heated in 9.1 ml of $POCl_3$ for 1.5 h. After removal of the solvent the residue was applied to silica gel column with AcOEt/n-hexane (3:7)) as eluent. Combination of the purified fractions and concentration in vacuo gave 0.31 g (13.8%) of the 4-chloro-6-fluoro-2-methyl-7-nitro-quinoline as brown solid. EI mass spectrum, m/e: 240.1(M calculated for $C_{10}H_6FN_2O_2$: 240).

A solution of 0.29 g (1.21 mmol) of 4-chloro-6-fluoro-2-methyl-7-nitro-quinoline in pyrrolidine (2 ml, 24 mmol) was heated at 80° C. (bath temperature) for 18 h. The excess pyrrolidine was removed in vacuo, the residue taken up in methylene chloride, which was washed with water, brine and then dried over magnesium sulfate. The solvent was removed in vacuo to give 0.34 g (79%) of the desired 2-methyl-7-nitro-4,6-di-pyrrolidin-1-yl-quinoline as dark red solid. ISP mass spectrum, m/e: 327.3 (M+1 calculated for $C_{18}H_{22}N_4O_2$: 327).

Example 71

In analogy to example 1, on reaction of 7-iodo-2-methyl-4-pyrrolidin-1-yl-quinoline with 3-amino-2-chloropyridine there was obtained: (2-choro-pyridin-3-yl)-(2-methyl-4-pyrrolidin-1-yl-quinolin-7-yl)-amine as brown foam. ISP mass spectrum, m/e: 339.3 (M+1 calculated for $C_{22}H_{24}ClN_3$: 339).

Example 72

In analogy to example 1, on reaction of (R)-7-iodo-4-(2-methoxymethyl-pyrrolidin-1-yl)-2-methyl-quinoline product of example 10b), with 4-aminobenzonitrile there was obtained: (R)-4-[4-(2-methoxymethyl-pyrrolidin-1-yl)-2-methyl-quinolin-7-ylamino]-benzonitrile as a light brown solid. ISP mass spectrum, m/e: 373.4 (M+1 calculated for $C_{23}H_{24}N_4O_0$: 373).

Example 73

In analogy to example 64, on reaction of (R)-7-iodo-4-(2-methoxymethyl-pyrrolidin-1-yl)-2-methyl-quinoline, product of example 10b), with 4-cyanobenzamide there was obtained: (R)-4-cyano-N-[4-(2-methoxymethyl-pyrrolidin-1-yl)-2-methyl-quinolin-7-yl]-benzamide as light brown solid. ISP mass spectrum, m/e: 401.5 (M+1 calculated for $C_{24}H_{24}N_4O_2$: 401).

Example 74

In analogy to example 64, on reaction of (R)-7-iodo-4-(2-methoxymethyl-pyrrolidin-1-yl)-2-methyl-quinoline product of example 10b), with acetamide there was obtained: (R)-N-[4-(2-methoxymethyl-pyrrolidin-1-yl)-2-methyl-quinolin-7-yl]-acetamide as light brown solid. ISP mass spectrum, m/e: 314.4 (M+1 calculated for $C_{18}H_{23}N_3O_2$: 314).

Example 75

In analogy to example 64, on reaction of (R)-7-iodo-4-(2-methoxymethyl-pyrrolidin-1-yl)-2-methyl-quinoline, product of example 10b), with 4-fluorobenzamide and conversion of the free base to the hydrochloride salt, there was obtained: (R)-4-fluoro-N-[4-(2-methoxymethyl-pyrrolidin-1-yl)-2-methyl-quinolin-7-yl]-benzamide hydrochloride as an off-white solid. ISP mass spectrum, m/e: 394.4 (M+1 calculated for $C_{23}H_{24}FN_3O_2$: 394).

Example 76

In analogy to example 1, on reaction of (S)-[1-(7-iodo-2-methyl-quinolin-4-yl)-pyrrolidin-2-yl]-methanol, product of example 53b), with 4-aminobenzonitrile there was obtained: (S)-4-[4-(2-hydroxymethyl-pyrrolidin-1-yl)-2-methyl-quinolin-7-ylamino]-benzonitrile as yellow solid. ISP mass spectrum, m/e: 359.3 (M+1 calculated for $C_{22}H_{22}N_4O$: 359).

Example 77

In analogy to example 1, on reaction of (S)-[1-(7-iodo-2-methyl-quinolin-4-yl)-pyrrolidin-2-yl]-methanol, product of example 53b), with 3-aminopyridine there was obtained: (S)-{1-[2-methyl-7-(pyridin-3-ylamino)-quinolin-4-yl]-pyrrolidin-2-yl}-methanol light brown solid. ISP mass spectrum, m/e: 335.3 (M+1 calculated for $C_{20}H_{22}N_4O$: 335).

Example 78

In analogy to example 47, on reaction of (S)-[1-(7-iodo-2-methyl-quinolin-4-yl)-pyrrolidin-2-yl]-methanol, product of example 53b), with 2-furamide there was obtained: (S)-furan-2-carboxylic acid [4-(2-hydroxymethyl-pyrrolidin-1-yl)-2-methyl-quinolin-7-yl]-amide as light yellow solid. ISP mass spectrum, m/e: 352.4 (M+1 calculated for $C_{20}H_{21}N_3O_3$: 352).

Example 79

In analogy to example 1, on reaction of (S)-[1-(7-iodo-2-methyl-quinolin-4-yl)-pyrrolidin-2-yl]-methanol, product of example 53b), with 3-amino-2-chloropyridine there was obtained: (S)-{1-[7-(2-chloro-pyridin-3-ylamino)-2-methyl-quinolin-4-yl]-pyrrolidin-2-yl}-methanol as an amorphous brown solid. ISP mass spectrum, m/e: 369.3 (M+1 calculated for $C_{20}H_{21}ClN_4O$: 369).

Example 80

In analogy to example 64, on reaction of (S)-[1-(7-iodo-2-methyl-quinolin-4-yl)-pyrrolidin-2-yl]-methanol, product of example 53b), with cyclopropyl carboxamide there was obtained: (S)-cyclopropanecarboxylic acid [4-(2-hydroxymethyl-pyrrolidin-1-yl)-2-methyl-quinolin-7-yl]-amide as an amorphous light brown solid. ISP mass spectrum, m/e: 326.3 (M+1 calculated for $C_{19}H_{23}N_3O_2$: 326).

Example 81

In analogy to example 64, on reaction of (S)-[1-(7-iodo-2-methyl-quinolin-4-yl)-pyrrolidin-2-yl]-methanol, product of example 53b), with 4-cyanobenzamide there was obtained: (S)-4-cyano-N-[4-(2-hydroxymethyl-pyrrolidin-1-yl)-2-methyl-quinolin-7-yl]-benzamide as a light yellow solid. ISP mass spectrum, m/e: 387.3 (M+1 calculated for $C_{23}H_{22}N_4O_2$: 387).

Example 82

In analogy to example 64, on reaction of (S)-[1-(7-iodo-2-methyl-quinolin-4-yl)-pyrrolidin-2-yl]-methanol product of example 53b), with 4-fluorobenzamide there was obtained: (S)-4-fluoro-N-[4-(2-hydroxymethyl-pyrrolidin-1-yl)-2-methyl-quinolin-7-yl]-benzamide as a light brown solid. ISP mass spectrum, m/e: 380.4 (M+1 calculated for $C_{22}H_{22}FN_3O_2$: 380).

Example 83

In analogy to example 1, on reaction of (S)-7-iodo-4-(3-methoxy-pyrrolidin-1-yl)-2-methyl-quinoline hydrochloride with 3-aminopyridine there was obtained: (S)-[4-(3-methoxy-pyrrolidin-1-yl)-2-methyl-quinolin-7-yl]-pyridin-3-yl-amine a brown foam. ISP mass spectrum, m/e: 335.4 (M+1 calculated for $C_{29}H_{22}N_4O$: 335).

Preparation of the Starting Material

In analogy to example 1b), on reaction of 4-chloro-7-iodo-2-methylquinoline with (S)-3-methoxy-pyrrolidine (2 mole equivalents) in 1-methyl-2-pyrrolidone as solvent at 140° C., and with conversion of the free base to the hydrochloride salt, there was obtained: (S)-7-iodo-4-(3-methoxy-pyrrolidin-1-yl)-2-methyl-quinoline hydrochloride an off-white solid. ISP mass spectrum, m/e: 369.2 (M+1 calculated for $C_{15}H_{17}IN_2O$: 369).

Example 84

In analogy to example 64, on reaction of (S)-7-iodo-4-(3-methoxy-pyrrolidin-1-yl)-2-methyl-quinoline hydrochloride, product of example 83b), with nicotinamide there was obtained: (S)-N-[4-(3-methoxy-pyrrolidin-1-yl)-2-methyl-quinolin-7-yl]-nicotinamide as a light brown solid. ISP mass spectrum, m/e: 365.2 (M+1 calculated for $C_{21}H_{22}N_4O_2$: 365).

Example 85

In analogy to example 64, on reaction of (S)-7-iodo-4-(3-methoxy-pyrrolidin-1-yl)-2-methyl-quinoline hydrochloride, product of example 83b), with propionamide there was obtained: (S)-N-[4-(3-methoxy-pyrrolidin-1-yl)-2-methyl-quinolin-7-yl]-propionamide as a light yellow solid. ISP mass spectrum, m/e: 314.4 (M+1 calculated for $C_{18}H_{23}N_3O_2$: 314).

Example 86

In analogy to example 64, on reaction of (S)-7-iodo-4-(3-methoxy-pyrrolidin-1-yl)-2-methyl-quinoline hydrochloride, product of example 83b), with 4-cyanobenzamide there was obtained: (S)-4-cyano-N-[4-(3-methoxy-pyrrolidin-1-yl)-2-methyl-quinolin-7-yl]-benzamide a brown solid. ISP mass spectrum, m/e: 387.3 (M+1 calculated for $C_{23}H_{22}N_4O_2$: 387).

Example 87

In analogy to example 64, on reaction of (S)-4-(3-ethoxy-pyrrolidin-1-yl)-7-iodo-2-methyl-quinoline hydrochloride with cyclopropyl carboxamide there was obtained: (S)-cyclopropanecarboxylic acid [4-(3-ethoxy-pyrrolidin-1-yl)-2-methyl-quinolin-7-yl]-amide as a light brown solid. ISP mass spectrum, m/e: 340.4 (M+1 calculated for $C_{20}H_{25}N_3O_2$: 340).

Preparation of the Starting Material

In analogy to example 1b), on reaction of 4-chloro-7-iodo-2-methylquinoline with (S)-3-ethoxy-pyrrolidine (2 mole equivalents) in 1-methyl-2-pyrrolidone as solvent at 140° C., with conversion of the free base to the hydrochloride salt, there was obtained: (S)-4-(3-ethoxy-pyrrolidin-1-yl)-7-iodo-2-methyl-quinoline hydrochloride an light brown solid solid. ISP mass spectrum, m/e: 383.2 (M+1 calculated for $C_{16}H_{19}IN_2O$: 383).

Example 88

In analogy to example 64, on reaction of (S)-4-(3-ethoxy-pyrrolidin-1-yl)-7-iodo-2-methyl-quinoline hydrochloride, product of example 87b), with 2-furylamide there was obtained: (S)-furan-2-carboxylic acid [4-(3-ethoxy-pyrrolidin-1-yl)-2-methyl-quinolin-7-yl]-amide as a white solid. ISP mass spectrum, m/e: 366.3 (M+1 calculated for $C_{21}H_{23}N_3O_2$: 366).

Example 89

In analogy to example 1, on reaction of (S)-4-(3-ethoxy-pyrrolidin-1-yl)-7-iodo-2-methyl-quinoline hydrochloride, product of example 87b), with 4-aminobenzonitrile there was obtained: (S)-4-[4-(3-ethoxy-pyrrolidin-1-yl)-2-methyl-quinolin-7-ylamino]-benzonitrile as a light yellow solid. ISP mass spectrum, m/e: 373.5 (M+1 calculated for $C_{23}H_{24}N_4O$: 373).

Example 90

In analogy to example 64, on reaction of (S)-4-(3-ethoxy-pyrrolidin-1-yl)-7-iodo-2-methyl-quinoline hydrochloride, product of example 87b), with nicotinamide there was obtained: (S)-N-[4-(3-ethoxy-pyrrolidin-1-yl)-2-methyl-quinolin-7-yl]-nicotinamide as a light brown solid. ISP mass spectrum, m/e: 377.4 (M+1 calculated for $C_{22}H_{24}N_4O_2$: 377).

Example 91

In analogy to example 1, on reaction of (S)-4-(3-ethoxy-pyrrolidin-1-yl)-7-iodo-2-methyl-quinoline hydrochloride, product of example 87b), with 4-aminopyridine there was obtained: (S)-[4-(3-ethoxy-pyrrolidin-1-yl)-2-methyl-quinolin-7-yl]-pyridin-3-yl-amine as a light brown solid. ISP mass spectrum, m/e: 349.5 (M+1 calculated for $C_{21}H_{24}N_4O$: 349).

Example 92

In analogy to example 64, on reaction of (S)-4-(3-ethoxy-pyrrolidin-1-yl)-7-iodo-2-methyl-quinoline hydrochloride, product of example 87b), with propionamide there was obtained: (S)-N-[4-(3-Ethoxy-pyrrolidin-1-yl)-2-methyl-quinolin-7-yl]-propionamide as a light brown solid. ISP mass spectrum, m/e: 328.4 (M+1 calculated for $C_{19}H_{25}N_3O_2$: 328).

Example 93

In analogy to example 64, on reaction of (S)-4-(3-ethoxy-pyrrolidin-1-yl)-7-iodo-2-methyl-quinoline hydrochloride, product of example 87b), with 2-fluorobenzamide there was obtained: (S)-N-[4-(3-ethoxy-pyrrolidin-1-yl)-2-methyl-quinolin-7-yl]-4-fluoro-benzamide as a light brown solid. ISP mass spectrum, m/e: 394.4 (M+1 calculated for $C_{23}H_{24}FN_3O_2$: 394).

Example 94

In analogy to example 64, on reaction of (S)-4-(3-ethoxy-pyrrolidin-1-yl)-7-iodo-2-methyl-quinoline hydrochloride, product of example 87b), with 4-cyanobenzamide, and with conversion of the free base to the hydrochloride salt, there was obtained: (S)-4-cyano-N-[4-(3-ethoxy-pyrrolidin-1-yl)-2-methyl-quinolin-7-yl]-benzamide hydrochloride as a light brown solid. ISP mass spectrum, m/e: 401.5 (M+1 calculated for $C_{24}H_{24}N_4O_2$: 401).

Example 95

In analogy to example 64, on reaction of (S)-4-(3-ethoxy-pyrrolidin-1-yl)-7-iodo-2-methyl-quinoline hydrochloride, product of example 87b), with 4-trimethylacetamide, and with conversion of the free base to the hydrochloride salt, there was obtained: (S)-N-[4-(3-ethoxy-pyrrolidin-1-yl)-2-methyl-quinolin-7-yl]-2,2-dimethyl-propionamide hydrochloride as a light brown solid. ISP mass spectrum, m/e: 356.4 (M+1 calculated for $C_{21}H_{29}N_3O_2$: 356).

Example 96

In analogy to example 64, on reaction of (S)-4-(3-ethoxy-pyrrolidin-1-yl)-7-iodo-2-methyl-quinoline hydrochloride, product of example 87b), with (4-chlorophenyl)-acetamide there was obtained: (S)-2-(4-chloro-phenyl)-N-[4-(3-ethoxy-pyrrolidin-1-yl)-2-methyl-quinolin-7-yl]-acetamide as a light brown solid. ISP mass spectrum, m/e: 424.5 (M+1 calculated for $C_{24}H_{26}N_3O_2Cl$: 424).

Example 97

In analogy to example 64, on reaction of (S)-4-(3-ethoxy-pyrrolidin-1-yl)-7-iodo-2-methyl-quinoline hydrochloride, product of example 87b), with (3-pyridyl)acetamide there was obtained: (S)-N-[4-(3-ethoxy-pyrrolidin-1-yl)-2-methyl-quinolin-7-yl]-2-pyridin-2-yl-acetamide a light brown solid. ISP mass spectrum, m/e: 391.2 (M+1 calculated for $C_{23}H_{26}N_4O_2$: 391).

Example 98

In analogy to example 64, on reaction of (S)-4-(3-ethoxy-pyrrolidin-1-yl)-7-iodo-2-methyl-quinoline hydrochloride, product of example 87b), with (4-methoxyphenyl)-acetamide there was obtained: (S)-N-[4-(3-ethoxy-pyrrolidin-1-yl)-2-methyl-quinolin-7-yl]-2-(4-methoxy-phenyl)-acetamide as a light brown solid. ISP mass spectrum, m/e: 420.4 (M+1 calculated for $C_{25}H_{29}N_3O_3$: 420).

Example 99

In analogy to example 64, on reaction of (S)-4-(3-ethoxy-pyrrolidin-1-yl)-7-iodo-2-methyl-quinoline hydrochloride, product of example 87b), with (3-trifluoromethyl-phenyl) acetamide there was obtained: (S)-N-[4-(3-ethoxy-pyrrolidin-1-yl)-2-methyl-quinolin-7-yl]-2-(3-trifluoromethyl-phenyl)-acetamide as a light brown solid. ISP mass spectrum, m/e: 458.5 (M+1 calculated for $C_{25}H_{26}F_3N_3O_2$: 458).

Example 100

In analogy to example 1, on reaction (S)-7-iodo-4-(2-methoxymethyl-pyrrolidin-1-yl)-2-methyl-quinoline with 4-aminobenzonitrile there was obtained: (S)-4-[4-(2-methoxy-methyl-pyrrolidin-1-yl)-2-methyl-quinolin-7-ylamino]-benzonitrile as a brown solid. ISP mass spectrum, m/e: 373.4 (M+1 calculated for $C_{23}H_{24}N_4O$: 373).
Preparation of the Starting Material
In analogy to example 1b), on reaction of 4-chloro-7-iodo-2-methylquinoline with (S)-2-(methoxymethyl) pyrrolidine there was obtained: (S)-7-iodo-4-(2-methoxymethyl-pyrrolidin-1-yl)-2-methyl-quinoline as a beige solid. ISP mass spectrum, m/e: 383.1 (M+1 calculated for $C_{16}H_{19}IN_2O$: 383).

Example 101

In analogy to example 1, on reaction (S)-7-iodo-4-(2-methoxymethyl-pyrrolidin-1-yl)-2-methyl-quinoline, product of example 100b), with 4-fluoroaniline there was obtained: (S)-(4-fluoro-phenyl)-[4-(2-methoxymethyl-pyrrolidin-1-yl)-2-methyl-quinolin-7-yl]-amine as an armorphous brown solid. ISP mass spectrum, m/e: 366.3 (M+1 calculated for $C_{22}H_{24}FN_3O$: 366).

Example 102

In analogy to example 1, on reaction (S)-7-iodo-4-(2-methoxymethyl-pyrrolidin-1-yl)-2-methyl-quinoline, product of example 100b), with 3-aminopyridine there was obtained: (S)-4-(2-methoxymethyl-pyrrolidin-1-yl)-2-methyl-quinolin-7-yl]-pyridin-3-yl-amine as a light yellow solid. ISP mass spectrum, m/e: 349.5 (M+1 calculated for $C_{21}H_{24}N_4O$: 349).

Example 103

In analogy to example 64, on reaction (S)-7-iodo-4-(2-methoxymethyl-pyrrolidin-1-yl)-2-methyl-quinoline, product of example 100b), with cyclopropyl carboxamide there was obtained: (S)-cyclopropanecarboxylic acid [4-(2-methoxymethyl-pyrrolidin-1-yl)-2-methyl-quinolin-7-yl]-amide as an amorphous brown solid. ISP mass spectrum, m/e: 340.3 (M+1 calculated for $C_{20}H_{25}N_3O_2$: 340).

Example 104

In analogy to example 64, on reaction (S)-7-iodo-4-(2-methoxymethyl-pyrrolidin-1-yl)-2-methyl-quinoline, product of example 100b), with trimethylacetamide there was obtained: (S)-N-[4-(2-methoxymethyl-pyrrolidin-1-yl)-2-methyl-quinolin-7-yl]-2,2-dimethyl-propionamide as an light brown solid. ISP mass spectrum, m/e: 356.3 (M+1 calculated for $C_{21}H_{29}N_3O_2$: 356).

Example 105

In analogy to example 1, on reaction (S)-7-iodo-4-(2-methoxymethyl-pyrrolidin-1-yl)-2-methyl-quinoline, product of example 100b), with cyclopropylmethylamine there was obtained: (S)-cyclopropylmethyl-[4-(2-methoxymethyl-pyrrolidin-1-yl)-2-methyl-quinolin-7-yl]-amine as a yellow foam. ISP mass spectrum, m/e: 326.5 (M+1 calculated for $C_{20}H_{27}N_3O$: 326).

Example 106

In analogy to example 64, on reaction (S)-7-iodo-4-(2-methoxymethyl-pyrrolidin-1-yl)-2-methyl-quinoline, product of example 100b), with propionamide there was obtained: (S)-N-[4-(2-methoxymethyl-pyrrolidin-1-yl)-2-methyl-quinolin-7-yl]-propionamide as an off-white solid. ISP mass spectrum, m/e: 328.4 (M+1 calculated for $C_{19}H_{25}N_3O_2$: 328).

Example 107

In analogy to example 64, on reaction (S)-7-iodo-4-(2-methoxymethyl-pyrrolidin-1-yl)-2-methyl-quinoline, product of example 100b), with 4-cyanobenzamide there was obtained: (S)-4-cyano-N-[4-(2-methoxymethyl-pyrrolidin-1-yl)-2-methyl-quinolin-7-yl]-benzamide as an light brown amorphous solid. ISP mass spectrum, m/e: 401.5 (M+1 calculated for $C_{24}H_{24}N_4O_2$: 401).

Example 108

In analogy to example 1, on reaction (S)-4-(2-ethoxymethyl-pyrrolidin-1-yl)-7-iodo-2-methyl-quinoline hydrochloride with 4-fluoroaniline and conversion of the free base to the hydrochloride, there was obtained: (S)-[4-(2-ethoxymethyl-pyrrolidin-1-yl)-2-methyl-quinolin-7-yl]-(4-fluoro-phenyl)-amine hydrochloride as an off-white solid. ISP mass spectrum, m/e: 380.3 (M+1 calculated for $C_{23}H_{26}FN_3O$: 380).
Preparation of the Starting Material:
A solution of 1.29 g (3.5 mmol) of (S)-[1-(7-iodo-2-methyl-quinolin-4-yl)-pyrrolidin-2-yl]-methanol, product of example 53b), in THF (40 ml) was treated at RT with 0.89 g (7.88 mmol) of potassium t-butylate, stirred for 30 minutes, and 0.636 ml (7.88 mmol) of ethyl iodide were added dropwise. After 2.5 h 0.25 ml of ethyl iodide were added and the reaction mixture was stirred at RT for 12 h. The mixture was partitioned between EtOAc and water, the layers separated, the organic layer dried over sodium sulphate and concentrated in vacuo. The residue was purified by flash chromatography on a silica gel column with was 3–5% MeOH in $CH_2Cl_2$ as eluent. Combination of the purified fractions, concentration in vacuo and conversion of the free base to the hydrochloride salt (on treatment with 1.25 M HCl in MeOH) gave 910 mg (60%) of the desired (S)-4-(2-ethoxymethyl-pyrrolidin-1-yl)-7-iodo-2-methyl-quinoline hydrochloride as a light yellow solid. ISP mass spectrum, m/e: 397.3 (M+1 calculated for $C_{17}H_{21}IN_2O$: 397).

Example 109

In analogy to example 1, on reaction of (S)-4-(2-ethoxymethyl-pyrrolidin-1-yl)-7-iodo-2-methyl-quinoline hydrochloride, product of example 108b), with 3-aminopyridine and preparation of the hydrochloride salt, there was obtained: (S)-[4-(2-ethoxymethyl-pyrrolidin-1-yl)-2-methyl-quinolin-7-yl]-pyridin-3-yl-amine hydrochloride as an light brown amorphous foam. ISP mass spectrum, m/e: 363.1 (M+1 calculated for $C_{22}H_{26}N_4O$: 363).

Example 110

In analogy to example 64, on reaction of (S)-4-(2-ethoxymethyl-pyrrolidin-1-yl)-7-iodo-2-methyl-quinoline hydrochloride, product of example 108b), with 2-furylamide and preparation of the hydrochloride salt, there was obtained: (S)-furan-2-carboxylic acid [4-(2-ethoxymethyl-pyrrolidin-1-yl)-2-methyl-quinolin-7-yl]-amide hydrochloride as an off-white solid. ISP mass spectrum, m/e: 380.3 (M+1 calculated for $C_{22}H_{25}N_3O_3$: 380).

Example 111

In analogy to example 1, on reaction of (R/S)-7-chloro-4-(2-methyl-1-pyrrolidinyl)-quinoline (Synthesis: 1995, p147) with 4-aminobenzonitrile—with the palladium complex SK-CC01-A (Solvias AG, Basel) instead of the $Pd(OAc)_2$/BINAP system—there was obtained: (R/S)-4-[4-(2-methyl-pyrrolidin-1-yl)-quinolin-7-ylamino]-benzonitrile as a light brown solid. ISP mass spectrum, m/e: 329.3 (M+1 calculated for $C_{21}H_{20}N_4$: 329).

Example 112

In analogy to example 1, on reaction (S)-4-(2-cyclopropylmethoxymethyl-pyrrolidin-1-yl)-7-iodo-2-methyl-quinoline hydrochloride with 4-aminobenzonitrile and conversion of the free base to the hydrochloride, there was obtained: (S)-4-[4-(2-cyclopropylmethoxymethyl-pyrrolidin-1-yl)-2-methyl-quinolin-7-ylamino]-benzonitrile hydrochloride as an off-white solid. ISP mass spectrum, m/e: 413.5 (M+1 calculated for $C_{26}H_{28}N_4O$: 413).
Preparation of the Starting Material:
In analogy to example 108b), on alkylation of (S)-[1-(7-iodo-2-methyl-quinolin-4-yl)-pyrrolidin-2-yl]-methanol, product of example 53b) with (bromomethyl)-cyclopropane and concersion of the free base to the hydrochloride there was obtained: (S)-4-(2-cyclopropylmethoxymethyl-pyrrolidin-1-yl)-7-iodo-2-methyl-quinoline hydrochloride as a light yellow solid. ISP mass spectrum, m/e: 423.3 (M+1 calculated for $C_{19}H_{23}IN_2O$: 423).

Example 113

In analogy to example 1, on reaction (S) 4-(2-cyclopropylmethoxymethyl-pyrrolidin-1-yl)-7-iodo-2-methyl-quinoline hydrochloride, product of example 112b), with 3-aminopyridine and conversion of the free base to the hydrochloride, there was obtained: (S)-[4-(2-cyclopropylmethoxymethyl-pyrrolidin-1-yl)-2-methyl-quinolin-7-yl]-pyridin-3-yl-amine hydrochloride as a brown foam. ISP mass spectrum, m/e: 389.2 (M+1 calculated for $C_{24}H_{28}N_4O$: 389).

Example 114

In analogy to example 64, on reaction of (R)-4-(3-ethoxy-pyrrolidin-1-yl)-7-iodo-2-methyl-quinoline hydrochloride with 4-cyanobenzamide there was obtained: (R)-4-cyano-N-[4-(3-ethoxy-pyrrolidin-1-yl)-2-methyl-quinolin-7-yl]-benzamide as a yellow solid. ISP mass spectrum, m/e: 401.4 (M+1 calculated for $C_{24}H_{24}N_4O_2$: 401).
Preparation of the Starting Material
In analogy to example 1b), on reaction of 4-chloro-7-iodo-2-methylquinoline with (R)-3-hydroxy-pyrrolidine (2.5 mole equivalents) in 1-methyl-2-pyrrolidone as solvent at 140° C., there was obtained: (R)-1-(7-iodo-2-methyl-quinolin-4-yl)-pyrrolidin-3-ol as an off-white solid. ISP mass spectrum, m/e: 355.2 (M+1 calculated for $C_{14}H_{15}IN_2O$: 355).
In analogy to example 108b), on alkylation of (R)-1-(7-iodo-2-methyl-quinolin-4-yl)-pyrrolidin-3-ol with ethyliodide and conversion of the free base to the hydrochloride there was obtained: (R)-4-(3-ethoxy-pyrrolidin-1-yl)-7-iodo-2-methyl-quinoline hydrochloride as a light brown solid. ISP mass spectrum, m/e: 383.2 (M+1 calculated for $C_{16}H_{19}IN_2O$: 383).

Example 115

In analogy to example 64, on reaction of (S)-4-(3-cyclopropylmethoxy-pyrrolidin-1-yl)-7-iodo-2-methyl-quinoline with nicotinamide there was obtained: (S)-N-[4-(3-cyclopropylmethoxy-pyrrolidin-1-yl)-2-methyl-quinolin-7-yl]-nicotinamide as a light yellow solid. ISP mass spectrum, m/e: 403.5 (M+1 calculated for $C_{24}H_{26}N_4O_2$: 403).
Preparation of the Starting Material
In analogy to example 1b), on reaction of 4-chloro-7-iodo-2-methylquinoline with (S)-3-hydroxy-pyrrolidine (2.5 mole equivalents) in 1-methyl-2-pyrrolidone as solvent at 140° C., there was obtained: (S)-1-(7-iodo-2-methyl-quinolin-4-yl)-pyrrolidin-3-ol as an light brown solid. ISP mass spectrum, m/e: 355.2 (M+1 calculated for $C_{14}H_{15}IN_2O$: 355).
In analogy to example 108b), on alkylation of (S)-1-(7-iodo-2-methyl-quinolin-4-yl)-pyrrolidin-3-ol with (bromomethyl)cyclopropane there was obtained: (S)-4-(3-cyclopropylmethoxy-pyrrolidin-1-yl)-7-iodo-2-methyl-quinoline as an orange oil. ISP mass spectrum, m/e: 409.2 (M+1 calculated for $C_{18}H_{21}IN_2O$: 409).

Example 116

In analogy to example 64, on reaction of 7-iodo-2,6-dimethyl-4-pyrrolidin-1-yl-quinoline with furan-2-carboxamide there was obtained: furan-2-carboxylic acid (2,6-dimethyl-4-pyrrolidin-1-yl-quinolin-7-yl)-amide as white foam. ISP-MS: m/e=336.3 ([M+H]$^+$).
Intermediates:

4-Chloro-7-iodo-2,6-dimethyl-quinoline

A suspension of 3-iodo-4-methylaniline (50.0 g, 215 mmol), ethyl acetoacetate (30.7 g, 236 mmol), and toluene-4-sulfonic acid monohydrate (430 mg, 2.15 mmol) was refluxed for 2 h in cyclohexane (100 mL), allowing the water formed to collect in a Dean-Stark trap, then after cooling insoluble material was removed by filtration and the filtrate evaporated. The residue was dissolved in Dowtherm® A (25 mL) and added dropwise to hot (ca. 250° C.) Dowtherm® A. After 15 min the reaction mixture was allowed to reach room temperature, then heptane (150 mL) was added and the precipitate collected by filtration. This material was triturated in ethyl acetate to afford a 1:1 mixture of 7-iodo-2,6-methyl-1H-quinolin-4-one and 5-iodo-2,6-dimethyl-1H-quinolin-4-one (46.4 g), which was treated with phosphorus oxide chloride (130 mL) and N,N-dimethylformamide (0.6 mL). The solution obtained was stirred at 50° C. for 20 min, then carefully poured upon ice and brought to pH 7 with 25% aq. ammonium hydroxide solution. After extraction with ethyl acetate, the organic layer was washed with brine, dried ($MgSO_4$), and evaporated. Recrystallization of the product mixture thus produced (4-chloro-7-iodo-2,6-dimethyl-quinoline and 4-chloro-5-iodo-2,6-dimethyl-quinoline) in hexane/ethyl acetate 9:1 (150 mL) afforded the title compound (7.55 g, 11%). Light brown solid, ISP-MS: m/e=318.1 ([M+H]$^+$).

7-Iodo-2,6-dimethyl-4-pyrrolidin-1-yl-quinoline

A solution of 4-chloro-7-iodo-2,6-dimethyl-quinoline (200 mg, 0.63 mmol) was refluxed in pyrrolidine (1.5 mL)

for 3 h. After evaporation of excess pyrrolidine, the residue was taken up in ethyl acetate and washed with 2 M aq. sodium hydroxide solution. The organic layer was washed with brine, dried (MgSO$_4$), and evaporated. Chromatography (SiO$_2$, CH$_2$Cl$_2$/MeOH/NH$_4$OH 95:5:0.25) afforded the title compound (193 mg, 87%). Light brown solid, ISP-MS: m/e=353.2 ([M+H]$^+$).

Example 117

In analogy to example 64, on reaction of 7-iodo-2,6-dimethyl-4-pyrrolidin-1-yl-quinoline with propionamide, there was obtained: N-(2,6-dimethyl-4-pyrrolidin-1-yl-quinolin-7-yl)-propionamide as light yellow foam. ISP-MS:: m/e=298.4 ([M+H]$^+$).

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example C

Tablets comprising the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example D

Capsules comprising the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example E

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:

1. A compound of formula

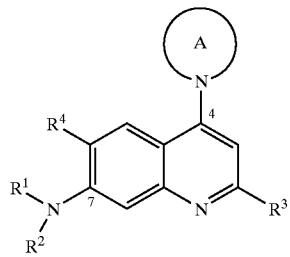

wherein

R$^1$ and R$^2$ are each independently substituted with hydrogen, alkyl, cycloalkyl, cycloalkylalkyl, alkylcarbonyl, cycloalkylcarbonyl, cycloalkylalkylcarbonyl, aryl, aralkyl, arylcarbonyl, aralkylcarbonyl, alkoxyalkyl, hydroxyalkyl, heterocyclyl, heterocyclylalkyl, heterocyclylcarbonyl, heterocyclylalkylcarbonyl, carbocyclyl, carbocyclylalkyl, amino, alkyl-SO$_2$—, aryl-SO$_2$—, heterocyclyl-SO$_2$— or amino-SO$_2$—, or R$^1$ and R$^2$ together with the N atom to which they are attached form a 5- to 10-membered heterocyclic ring which optionally comprises a second heteroatom selected from nitrogen or oxygen and wherein the heterocyclyc ring is optionally substituted with one or more substituents independently selected from the group consisting of alkyl and alkoxy;

R$^3$ is hydrogen, alkyl, amino or halogen;

R$^4$ is hydrogen, halogen, heterocyclyl, amino or alkyl;

A is a 5 to 7-membered saturated heterocyclic ring comprising the nitrogen atom which is attached to the quinoline ring and optionally a second heteroatom which is selected from oxygen, sulfur or nitrogen and, wherein the ring A is optionally substituted by one to three substituents independently selected from the group consisting of alkyl, alkoxy, hydroxy, amino, acetylamino, cyano, hydroxyalkyl, alkoxyalkyl, cycloalkylalkoxy and cycloalkylalkoxyalkyl;

and pharmaceutically acceptable salts and esters thereof.

2. The compounds according to claim 1, wherein

R$^1$ and R$^2$ are each independently substituted with hydrogen, alkyl, cycloalkyl, cycloalkylalkyl, alkylcarbonyl, cycloalkylcarbonyl, aryl, aralkyl, arylcarbonyl, alkoxyalkyl, hydroxyalkyl, heterocyclyl, heterocyclylalkyl, heterocyclylcarbonyl, carbocyclyl, carbocyclylalkyl, amino, alkyl-$SO_2$—, aryl-$SO_2$—, heterocyclyl-$SO_2$— or amino-$SO_2$— or $R^1$ and $R^2$ together with the N atom to which they are attached form a 5- to 10-membered heterocyclic ring which optionally comprises a second heteroatom selected from nitrogen or oxygen and, wherein the heterocyclyc ring is optionally substituted with one or more substituents independently selected from alkyl and alkoxy; and A is a 5 to 7-membered saturated heterocyclic ring comprising the nitrogen atom which is attached to the quinoline ring and optionally a second heteroatom which is selected from oxygen, sulfur or nitrogen and, wherein the ring A is optionally substituted by one to three substituents independently selected from alkyl, alkoxy, hydroxy, amino, acetylamino, cyano, hydroxyalkyl and alkoxyalkyl.

3. The compound according to claim 1, wherein $R^1$ and $R^2$ are each independently hydrogen, alkyl, cycloalkyl, cycloalkylalkyl, alkylcarbonyl, cycloalkylcarbonyl, aryl, aralkyl, arylcarbonyl, alkoxyalkyl, hydroxyalkyl, heterocyclyl, heterocyclylalkyl, heterocyclylcarbonyl, carbocyclyl, carbocyclylalkyl, amino, alkyl-$SO_2$—, aryl-$SO_2$—, heterocyclyl-$SO_2$— or amino-$SO_2$—.

4. The compound according to claim 3 wherein one of $R^1$ or $R^2$ is hydrogen or alkyl.

5. The compounds according to claim 1, wherein $R^1$ and $R^2$ together with the N atom to which they are attached form a 5- to 10-membered heterocyclic ring which optionally comprises a second heteroatom selected from nitrogen or oxygen and, wherein the heterocyclyc ring is optionally substituted with one or more substituents independently selected from alkyl and alkoxy.

6. The compound according to claim 5, wherein A is pyrrolidine or azepane optionally substituted with alkyl, alkoxyalkyl, hydroxyalkyl or alkoxy.

7. The compound according to claim 1, wherein $R^3$ is hydrogen or alkyl.

8. The compound according to claim 7, wherein $R^3$ is methyl.

9. The compound according to claim 1, wherein $R^4$ is hydrogen.

10. The compound according to claim 1, wherein $R^4$ is amino.

11. The compound according to claim 1, wherein $R^4$ is pyrrolidinyl.

12. The compound according to claim 1, wherein A is pyrrolidine or azepane optionally substituted with alkyl, alkoxyalkyl, hydroxyalkyl or alkoxy.

13. The compound according to claim 12, wherein A is pyrrolidine optionally substituted with hydroxymethyl or methoxymethyl.

14. The ompound according to claim 1, wherein $R^1$ and $R^2$ together with the N atom to which they are attached form an azepane-, a 3,4-dihydro-1H-isoquinoline-, a piperidine-, a pyrrolidine- or a morpholine ring which are optionally substituted with one to three substituents independently selected from alkyl and alkoxy.

15. The compound according to 1, wherein one of $R^1$ and $R^2$ is hydrogen or alkyl and the other is alkyl, cycloalkyl, cycloalkylalkyl, alkylcarbonyl, cycloalkylcarbonyl, phenyl, naphthyl, phenylalkyl, naphthylalkyl, phenylcarbonyl, alkoxyalkyl, hydroxyalkyl, thiophenyl, pyridinyl, furyl, thiophenylalkyl, pyridinylalkyl, furylalkyl, thiophenylcarbonyl, pyridinylcarbonyl, furylalkyl, indanyl, carbocyclylalkyl, amino, alkyl-$SO_2$—, aryl-$SO_2$—, thiophenyl-$SO_2$—, pyridinyl-$SO_2$—, furyl-$SO_2$—, or amino-$SO_2$—, and, wherein the phenyl and naphthyl groups of are optionally each independently further substituted with alkyl, cyano, halogeno, alkoxy or trifluoromethyl.

16. The compound according to 15, wherein one of $R^1$ and $R^2$ is hydrogen or methyl and the other is alkylcarbonyl, cycloalkylcarbonyl, cyanophenyl, alkoxybenyl, cyanophenylcarbonyl, fluorophenylcarbonyl, thiophenylalkyl, pyridinylcarbonyl, furylcarbonyl, alkyl-$SO_2$—, pyridyl-$SO_2$—, pyridinyl or cycloalkylcarbonyl.

17. The compound according to claim 15, wherein A is pyrrolidine or azepane optionally substituted with alkyl, alkoxyalkyl, hydroxyalkyl or alkoxy.

18. The compound according to claim 1 selected from the group consisting of
cyclopropanecarboxylic acid (2-methyl-4-pyrrolidin-1-yl-quinolin-7-yl)-amide;
2,2-dimethyl-N-(2-methyl-4-pyrrolidin-1-yl-quinolin-7-yl)-propionamide;
4-(2-methyl-4-pyrrolidin-1-yl-quinolin-7-ylamino)-benzonitrile;
3-methyl-N-(2-methyl-4-pyrrolidin-1-yl-quinolin-7-yl)-butyramide;
isobutyl-(2-methyl-4-pyrrolidin-1-yl-quinolin-7-yl)-amine;
N-(2-methyl-4-pyrrolidin-1-yl-quinolin-7-yl)-nicotinamide;
(2,2-dimethyl-propyl)-(2-methyl-4-pyrrolidin-1-yl-quinolin-7-yl)-amine;
4-cyano-N-(2-methyl-4-pyrrolidin-1-yl-quinolin-7-yl)-benzamide;
(2-methoxy-benzyl)-(2-methyl-4-pyrrolidin-1-yl-quinolin-7-yl)-amine;
(2-methyl-4-pyrrolidin-1-yl-quinolin-7-yl)-thiophen-2-ylmethyl-amine;
4-fluoro-N-(2-methyl-4-pyrrolidin-1-yl-quinolin-7-yl)-benzamide;
N-(2-methyl-4-pyrrolidin-1-yl-quinolin-7-yl)-isonicotinamide;
(S)-N-[4-(2-hydroxymethyl-pyrrolidin-1-yl)-2-methyl-quinolin-7-yl]-nicotinamide;
N-methyl-N-(2-methyl-4-pyrrolidin-1-yl-quinolin-7-yl)-nicotinamide;
(S)-furan-2-carboxylic acid [4-(2-hydroxymethyl-pyrrolidin-1-yl)-2-methyl-quinolin-7-yl]-amide;
N-(2-methyl-4-pyrrolidin-1-yl-quinolin-7-yl)-methanesulfonamide;
pyridine-3-sulfonic acid (2-methyl-4-pyrrolidin-1-yl-quinolin-7-yl)-amide;
(R)-4-[4-(2-methoxymethyl-pyrrolidin-1-yl)-2-methyl-quinolin-7-ylamino]-benzonitrile;
(S)-4-[4-(2-hydroxymethyl-pyrrolidin-1-yl)-2-methyl-quinolin-7-ylamino]-benzonitrile;
(S)-[4-(3-methoxy-pyrrolidin-1-yl)-2-methyl-quinolin-7-yl]-pyridin-3-yl-amine;
(S)-cyclopropanecarboxylic acid [4-(3-ethoxy-pyrrolidin-1-yl)-2-methyl-quinolin-7-yl]-amide;
(S)-4-[4-(3-ethoxy-pyrrolidin-1-yl)-2-methyl-quinolin-7-ylamino]-benzonitrile;
(S)-[4-(3-ethoxy-pyrrolidin-1-yl)-2-methyl-quinolin-7-yl]-pyridin-3-yl-amine;
(S)-N-[4-(3-Ethoxy-pyrrolidin-1-yl)-2-methyl-quinolin-7-yl]-propionamide;

(S)-cyclopropanecarboxylic acid [4-(2-methoxymethyl-pyrrolidin-1-yl)-2-methyl-quinolin-7-yl]-amide;
furan-2-carboxylic acid (2,6-dimethyl-4-pyrrolidin-1-yl-quinolin-7-yl)-amide; and
N-(2,6-dimethyl-4-pyrrolidin-1-yl-quinolin-7-yl)-propionamide.

19. A pharmaceutical composition for the promotion of weight reduction comprising a compound in accordance with claim 1 in an amount effective to reduce appetite and a therapeutically inert carrier.

20. A method for the treatment of obesity in humans comprising administering the composition in accordance with claim 19 in a dosage effective to reduce appetite.

21. The method of claim 20 further comprising the administration of a lipase inhibitor.

22. The method according to claim 21, wherein the lipase inhibitor is orlistat.

* * * * *

UNITED STATES PATENT AND TRADEMARK OFFICE
CERTIFICATE OF CORRECTION

PATENT NO.   : 6,696,467 B2
DATED        : February 24, 2004
INVENTOR(S)  : Patrizio Mattei et al.

It is certified that error appears in the above-identified patent and that said Letters Patent is hereby corrected as shown below:

<u>Column 44,</u>
Line 65, "The compounds…" should be -- The compound… --

<u>Column 45,</u>
Line 31, "The compounds…" should be -- The compound… --
Line 57, "The ompound…" should be -- The compound… --

<u>Column 48,</u>
Line 8, "…inhibitor is orlistat." should be -- …inhibitor is (1S)-1-[[(2S,3S)-3-hexyl-4-oxo-2-oxetanyl]methyl]dodecylester N-formyl-L-leucine. --

Signed and Sealed this

Twenty-second Day of June, 2004

JON W. DUDAS
*Acting Director of the United States Patent and Trademark Office*